US012790537B2

(12) United States Patent
Kukkonen et al.

(10) Patent No.: US 12,790,537 B2
(45) Date of Patent: Nov. 10, 2026

(54) TAGGING AGENTS, ANTI-SCALANT POLYMER COMPOSITIONS, AND METHODS

(71) Applicant: Sterling Specialty Chemicals Holding UK Limited, Harrow (GB)

(72) Inventors: Viktor Kukkonen, Espoo (FI); Salla Puupponen, Espoo (FI); Vesa Nuutinen, Helsinki (FI); Erkki-Johannes Metsälä, Helsinki (FI)

(73) Assignee: Sterling Specialty Chemicals Holding UK Limited, Harrow (GB)

( * ) Notice: Subject to any disclaimer, the term of this patent is extended or adjusted under 35 U.S.C. 154(b) by 683 days.

(21) Appl. No.: 18/248,196

(22) PCT Filed: Jun. 1, 2021

(86) PCT No.: PCT/US2021/035144
§ 371 (c)(1),
(2) Date: Apr. 6, 2023

(87) PCT Pub. No.: WO2022/076041
PCT Pub. Date: Apr. 14, 2022

(65) Prior Publication Data

US 2024/0124768 A1 Apr. 18, 2024

Related U.S. Application Data

(60) Provisional application No. 63/088,655, filed on Oct. 7, 2020.

(51) Int. Cl.
*C09K 11/06* (2006.01)
*C02F 5/10* (2023.01)
(Continued)

(52) U.S. Cl.
CPC ................ *C09K 11/06* (2013.01); *C02F 5/10* (2013.01); *C07D 311/82* (2013.01);
(Continued)

(58) Field of Classification Search
None
See application file for complete search history.

(56) References Cited

U.S. PATENT DOCUMENTS 4,304,720 A * 12/1981 Dean .................... C07D 311/82 558/8
5,102,785 A 4/1992 Livak et al.
(Continued)

FOREIGN PATENT DOCUMENTS

EP 0485882 A1 5/1992
JP 2010-139784 A 6/2010
(Continued)

OTHER PUBLICATIONS

Popov et al. (Journal of Applied Polymer Science, 2017, pp. 1-11). (Year: 2017).*
(Continued)

*Primary Examiner* — Clare M Perrin
(74) *Attorney, Agent, or Firm* — Dilworth IP, LLC

(57) ABSTRACT

Tagging agents, including fluorescent monomers, which may lack polymerizable double bonds. Anti-scalant polymer compositions that include a copolymer of a tagging agent and an anti-scalant monomer. Methods for synthesizing tagging agents, anti-scalant polymer compositions, and detecting an anti-scalant polymer composition.

6 Claims, 2 Drawing Sheets

(51) Int. Cl.

| | |
|---|---|
| ***C07D 311/82*** | (2006.01) |
| ***C08F 222/06*** | (2006.01) |
| ***C09B 69/10*** | (2006.01) |

(52) U.S. Cl.

CPC .......... *C08F 222/06* (2013.01); *C09B 69/103* (2013.01); *C08F 2810/40* (2013.01); *C09K 2211/145* (2013.01)

(56) References Cited

U.S. PATENT DOCUMENTS

| | | | | |
|---|---|---|---|---|
| 5,410,053 | A * | 4/1995 | Hahn | C09D 11/50 8/510 |
| 5,637,733 | A | 6/1997 | Sujeeth | |
| 5,851,621 | A | 12/1998 | Wolleb et al. | |
| 7,943,058 | B2 | 5/2011 | Hills et al. | |
| 8,227,381 | B2 | 7/2012 | Rodrigues et al. | |
| 2001/0001800 | A1 | 5/2001 | Nagano et al. | |
| 2001/0018503 | A1 * | 8/2001 | Whipple | C08F 246/00 526/287 |
| 2003/0183575 | A1 | 10/2003 | Zeiher et al. | |
| 2010/0130505 | A1 | 5/2010 | Smrcka et al. | |
| 2016/0185636 | A1 | 6/2016 | Musale et al. | |

FOREIGN PATENT DOCUMENTS

| | | | |
|---|---|---|---|
| WO | 2005000747 | A2 | 1/2005 |
| WO | 2006078847 | A2 | 7/2006 |
| WO | 2011090101 | A1 | 7/2011 |
| WO | 2014009445 | A1 | 1/2014 |

OTHER PUBLICATIONS

International Search Report and Written Opinion issued in international application No. PCT/US2021/035144, mailed Oct. 14, 2021, 10 pages.

Popov et al., Synthesis and properties of novel fluorescent-tagged polyacrylate-based scale inhibitors, Journal of Applied Polymer Science, Jul. 10, 2017, vol. 134, p. 1-11, p. 1, abstract, figure listed, p. 2, Scheme 2.

Opinion on Patentability issued in Finnish application No. 20206073, dated Apr. 30, 2021, 9 pages.

Beija, M., et al., "Novel Malachite Green- and Rhodamine B-labeled cationic chain transfer agents for RAFT polymerization", Polymer, vol. 52, No. 26, Dec. 13, 2011, pp. 5933-5946.

Partial Supplementary European Search Report and Search Opinion received for EP Application No. 21878156.5, mailed on Oct. 24, 2024, 14 pages.

Office Action issued in App. No. SA523440274, 8 pages.

* cited by examiner

TAGGING AGENTS, ANTI-SCALANT POLYMER COMPOSITIONS, AND METHODS

FIELD OF THE INVENTION

This disclosure is directed to tagging agents and polymeric, detectable water treatment chemical compositions, including anti-scalant polymer compositions.

BACKGROUND

Polymeric water treatment chemicals are used in various applications, such as scale inhibitors in squeeze treatment, cooling water towers, desalination etc. In some, if not all, of these applications, it is necessary or desirable to know a concentration of a polymer in a fluid, such as water.

Current methods for determining the concentration of a polymeric water treatment chemical include the direct and indirect measurement of polymer concentration. Indirect measurement of polymer concentration may be achieved by elemental analysis, such as measuring phosphorous from a polymer, or the fluorescence intensity of a polymer. The fluorescence-based technique can be implemented by adding a fluorescence tracer into a polymer and/or by incorporating a fluorescent tag monomer into a polymer via polymerization.

In desalination, cooling, and boiler water applications, polyacrylates are the most widely-used scale inhibitors. The tagging of polyacrylates, however, is limited mainly to sodium styrene sulfonate (NaSS) monomers. This tag chemistry has a relatively low fluorescence yield, and, as a result, the concentration of NaSS in a final product must be relatively high (e.g., greater than 2 wt-%). A relatively higher tag concentration may be disadvantageous for one or more reasons. For example, the product cost may be greater, the scale inhibition performance may be negatively impacted, or a combination thereof.

Previous efforts to incorporate fluorescent tags into polymers have relied on fluorescent tags that include a polymerizable double bond. This feature, however, is not common in many dyes, especially commercially available dyes. A number of dyes, therefore, could not be used as a fluorescent tag in previous methods. U.S. Patent Application Publication No. 2001/018503A and PCT Publication No. WO2014/009445A1 disclose fluorescent tag molecules which contain a polymerizable double bond that can be used for attaching the tag to a polymer chain. It is also known that there are fluorescence tags, which attach to another molecule, such as a protein, by click-chemistry, by condensation, or by addition to an activated double bond without a radical reaction (see, e.g., U.S. Pat. Nos. 5,216,086, and 5,772,894).

There remains a need for compounds, compositions, and methods for detecting or quantifying relatively low levels (e.g., at ppm scale) of polymers that overcome one or more of the foregoing disadvantages, including compounds, compositions, and methods that eliminate the need for a fluorescent tag that includes a polymerizable double bond.

BRIEF SUMMARY

Provided herein are compounds, including compounds that lack a polymerizable double bond, which may be used as fluorescent tagging agents. It was surprisingly discovered that the compounds provided herein, which include xanthene derivatives, could be used to tag a polymer, despite the compounds' lack of a polymerizable double bond. The compounds provided herein may bond to a polymer via radical reaction.

Due to the fact that a polymerizable double bond is not a necessary feature of embodiments of the compounds described herein, the compositions and methods herein may use numerous commercially available dyes as fluorescent tagging agents. In some embodiments, the compounds herein include xanthene derivatives, which may exhibit a desirable fluorescence yield, thereby allowing a polymer composition to be tagged with a very low concentration of a compound (e.g., sub ppm).

In some embodiments, the compounds described herein, which may include fluorescein or fluorescein derivatives, can tolerate oxidative polymerization conditions in acid without forming non-fluorescent compounds. In some embodiments, the compounds described herein, which may include rhodamine or rhodamine derivatives, can tolerate alkaline conditions without oxidizing. In some embodiments, the compounds described herein can reversibly form a non-fluorescent compound in oxidative polymerization conditions, but the non-fluorescent compound can be reversibly transformed back to fluorescent compound.

In some embodiments, the compounds provided herein can be polymerized with dispersing agents, anti-scalants, polymers, and/or other materials that may benefit from the presence of a controllable tag. The compounds provided herein and their derivatives (e.g., polymer derivatives) may be suitable for a number of applications, including, but not limited to, oil field anti-scalants, dispersing agents, and/or scale-controlling agents, which may optionally be used in cooling towers. The compounds provided herein and/or derivatives thereof may be used as biomarkers.

In one aspect, compounds are provided which may be used as tagging agents, including fluorescent tagging agents. In some embodiments, the compounds include a compound or isomer of Formula (I):

Formula (I)

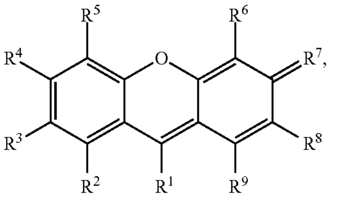

wherein $R^1$ is selected from the group consisting of hydrogen, hydroxyl, and a hydrocarbyl (e.g., aryl or alkyl) optionally substituted with one or more functional groups, such as a carboxylic acid moiety or sulfonic acid moiety, with the proviso that the hydrocarbyl does not include any double bonds that (i) are non-conjugated and (ii) form a direct covalent bond between two carbon atoms; wherein $R^4$ is selected from the group consisting of hydroxyl and —NR'R"; wherein $R^7$ is selected from the group consisting of oxygen, —NR'R", and —NR'; wherein $R^2$, $R^3$, $R^5$, $R^6$, $R^8$, and $R^9$ are independently selected from the group consisting of hydrogen, hydroxyl, alkoxy, —N(R')(R"), alkyl, aryl, and halogen; and wherein R' and R" are independently selected from the group consisting of hydrogen and alkyl. Preferably, at least one of $R^3$, $R^5$, $R^6$ and $R^8$ is hydrogen. In some embodiments, none of $R^1$, $R^2$, $R^3$, $R^4$, $R^5$, $R^6$, $R^7$, $R^8$, and $R^9$ includes (a) any double bonds, or (b) any double bonds that (i) are non-conjugated and (ii) form a direct covalent bond between two carbon atoms. In some embodiments, none of $R^1$, $R^2$, $R^3$, $R^5$, $R^6$, $R^8$, and $R^9$ includes (a) any double bonds, or (b) any double bonds that (i) are non-conjugated and (ii) form a direct covalent bond between two carbon atoms. In some embodiments, $R^1$ does not include any double bonds.

In another aspect, polymer compositions are provided. In some embodiments, the polymer compositions are scale-inhibiting polymer compositions. The polymer compositions may include a copolymer. The copolymer may include a first monomer that is a tagging agent, and at least one second monomer that is an anti-scalant (e.g., the at least one second monomer includes functional groups effective for scale inhibition). In some embodiments, the copolymer includes a first monomer selected from a compound or isomer of Formula (I), wherein the first monomer is a tagging monomer. In some embodiments, the copolymer includes (i) a first monomer selected from the group consisting of a compound or isomer of Formula (I), a salt, a hydrate, a salt hydrate, a stereoisomer, a dehydrate, a tautomer, or a derivative thereof, wherein the first monomer is a tagging monomer, and (ii) at least one second monomer that includes at least one polymerizable double bond or at least one polymerizable triple bond, wherein the at least one second monomer is a scale-inhibiting monomer.

In yet another aspect, methods of synthesizing compounds and anti-scalant polymer compositions are provided. In some embodiments, the methods of synthesizing the compounds include a polycondensation reaction. A polycondensation reaction may include contacting an aryl alcohol (e.g., a phenol or an amino-substituted aryl alcohol (e.g., an aminophenol)), a condensation catalyst, and a compound according to Formula (A) or Formula (B) to form the condensation product;

Formula (A)

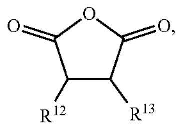

Formula (B)

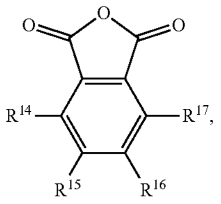

wherein $R^{12}$, $R^{13}$, $R^{14}$, $R^{15}$, $R^{16}$, and $R^{17}$ are independently selected from the group consisting of hydrogen, hydroxyl, and alkyl (e.g., $C_1$-$C_6$ alkyl). In some embodiments, the methods include polymerizing a compound, such as a condensation product. The methods of polymerization may include contacting a compound, including a condensation product of the methods herein, with at least one second monomer to form a copolymer; wherein the at least one second monomer includes a polymerizable double bond and/or a polymerizable triple bond.

In a still further aspect, methods for preventing or reducing scale formation are provided. In some embodiments, the methods include providing a system that includes a fluid in circulation, wherein the fluid includes a scale-inhibiting polymer composition as described herein; and measuring with an analytical technique an amount of a tagging agent monomer in the system or the fluid, wherein the measuring is performed periodically or continuously. Measuring the amount of a tagging agent monomer in the system or the fluid may permit the amount of a scale-inhibiting polymer composition that is present in the system or the fluid to be determined. The methods also may include regulating an amount of a scale-inhibiting polymer composition in a system or a fluid. For example, the methods also may include adding an additional amount of a scale-inhibiting polymer composition to the system or the fluid if the amount of the scale-inhibiting polymer composition in the system or the fluid is less than a predetermined value. The methods also may include removing an amount of a scale-inhibiting polymer composition in a system or a fluid if the amount of the scale-inhibiting polymer composition in the system or the fluid is greater than a predetermined value.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
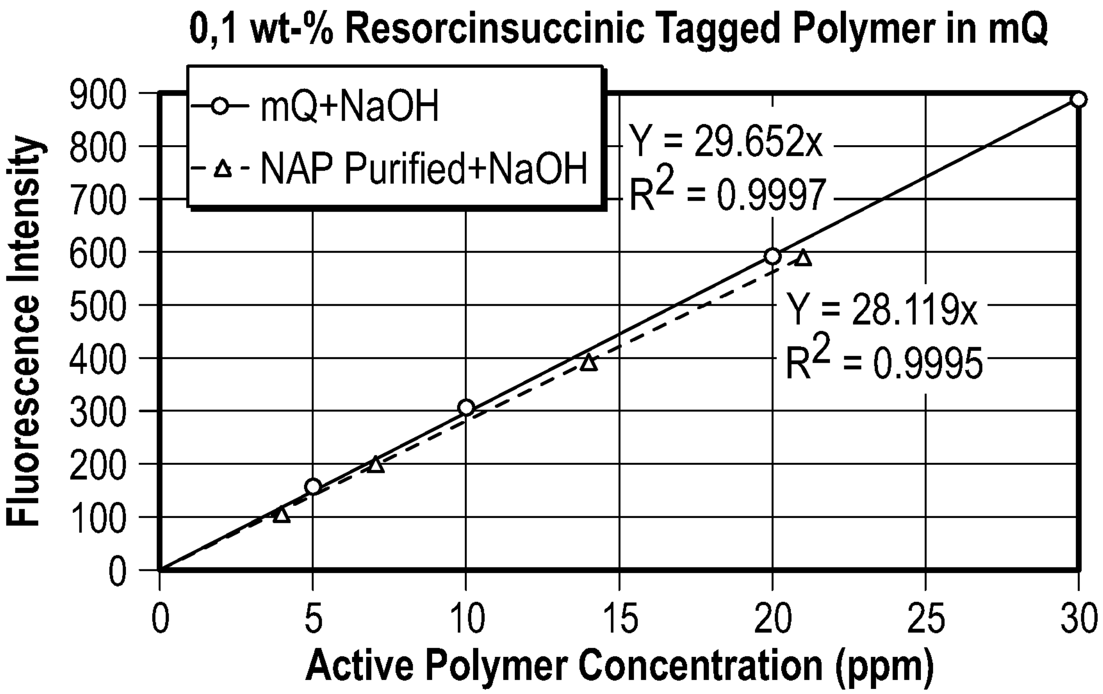
FIG. 1 depicts fluorescence emission maxima of one embodiment of a polymer tagged with an embodiment of a tagging agent described herein.

Provided herein are compounds that may be used as tagging agents, polymers that include the compounds as a monomer (e.g., a comonomer and/or end group), polymer compositions, including scale-inhibiting polymer compositions, that include the polymers, methods for forming the compounds and polymers, and methods for monitoring a concentration of the compounds, polymers, or polymer compositions.

Compounds

Compounds are provided herein, which may be used as fluorescent tagging monomers in polymers, including those disclosed herein. As used herein, the phrases "tagging agent", "tagging monomer", and the like refer to a compound and/or monomer that is detectable at a desirable concentration (e.g., a relatively low concentration) using an analytical technique, such as fluorescence spectroscopy. The tagging monomers provided herein, in some embodiments, exhibit a fluorescence emission maximum at about 300 nm to about 800 nm, about 350 nm to about 750 nm, about 400 nm to about 700 nm, about 410 nm to about 680 nm, about 410 nm to about 600 nm, about 410 nm to about 590 nm, about 410 nm to about 520 nm, about 410 nm to about 500 nm, about 440 nm to about 450 nm, about 500 nm to about 520 nm, about 550 nm to about 590 nm, about 640 nm to about 680 nm, or about 570 nm to about 600 nm, thereby providing polymer compositions or other products with a feature that may permit an amount (e.g., a concentration) of a polymer composition that includes a tagging monomer to be monitored. In some embodiments, the excitation and emission wavelengths are determined, and, therefore, may be adjusted, by selecting a particular arylalcohol/amino aryl alcohol. The fluorescence emission may be affected by pH; for example, the keto-enol tautomers described herein may exhibit different fluorescence emissions.

The compounds, including tagging monomers, provided herein include compounds or isomers of Formula (I). The phrase "compound of Formula (I)", the term "compound" when it refers to Formula (I), the term "isomer" when it refers to Formula (I), and the like, as used herein, refer to and include compounds according to or isomers of, respectively, the structures of each formula, salts thereof, hydrates thereof, salt hydrates thereof, stereoisomers thereof, dehydrates thereof, and derivatives thereof. Therefore, the formulas and structures provided herein encompass and read on the formulas and structures as drawn or isomers of the formulas and structures as drawn, as well as salts, hydrates, salt hydrates, stereoisomers, dehydrates, tautomers, protonated/deprotonated forms, or derivatives of each formula and structure or isomer thereof. The "derivatives" of each formula and structure include, but are not limited, to polymers (e.g., oligomers, copolymers, etc.) formed of the compounds. The tautomers may include keto-enol tautomers.

The compounds provided herein include compounds or isomers of Formula (I), which, as explained herein, include salts, hydrates, salt hydrates, stereoisomers, dehydrates, tautomers, and derivatives of the compounds or isomers of Formula (I):

Formula (I)

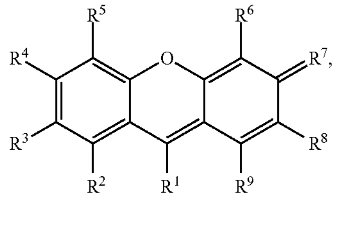

wherein $R^1$ is selected from the group consisting of hydrogen, hydroxyl, and a hydrocarbyl (e.g., alkyl or aryl) optionally substituted with one or more functional groups, such as a carboxylic acid moiety or a sulfonic acid moiety, with the proviso that the hydrocarbyl does not include any double bonds that (i) are non-conjugated and (ii) form a direct covalent bond between two carbon atoms; wherein $R^4$ is selected from the group consisting of hydroxyl and —NR'R"; wherein $R^7$ is selected from the group consisting of oxygen, —NR'R", and —NR'; wherein $R^2$, $R^3$, $R^5$, $R^6$, $R^8$, and $R^9$ are independently selected from the group consisting of hydrogen, hydroxyl, alkoxy, —N(R')(R"), alkyl, aryl, and halogen; and wherein R' and R" are independently selected from the group consisting of hydrogen and alkyl. In some embodiments, none of $R^1$, $R^2$, $R^3$, $R^4$, $R^5$, $R^6$, $R^7$, $R^8$, and $R^9$ includes (i) any double bonds or (ii) any double bonds that (a) are non-conjugated and (b) form a direct covalent bond between two carbon atoms.

In some embodiments, a hydrocarbyl is a $C_1$-$C_{30}$ hydrocarbyl, a $C_1$-$C_{20}$ hydrocarbyl, or a $C_1$-$C_{10}$ hydrocarbyl. In some embodiments, alkoxy is a $C_1$-$C_6$ alkoxy. In some embodiments, alkyl is a $C_1$-$C_6$ alkyl. In some embodiments, aryl is a $C_4$-$C_{14}$ aryl.

The term "hydrocarbyl", as used herein, generally refers to alkyl, aryl, or arylalkyl groups. The phrase "$C_1$-$C_{10}$ hydrocarbyl" and the like, as used herein, generally refers to alkyl, aryl, or arylalkyl groups containing 1 to 10 carbon atoms. The 1 to 10 carbon atoms include the carbon atoms of any substituents, such as a carbon atom of a carboxylic acid moiety. Examples of alkyl groups, in each instance, include, but are not limited to, a non-cyclic group, a cycloalkyl group, and the like, and includes all substituted, unsubstituted, branched, and linear analogs or derivatives thereof. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, cycloheptanyl, and adamantyl. Additional examples of alkyl moieties have linear, branched and/or cyclic portions (e.g., 1-ethyl-4-methyl-cyclohexyl). Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof.

As used herein, a "conjugated double bond" is a double bond that is separated from a second double bond by one single bond. An example of a "conjugated double bond" is an aryl double bond, which is a covalent bond between two atoms that are both members of an aromatic ring, such as benzene. All other double bonds are "non-conjugated" double bonds. The following structure depicts an example of an aryl double bond, which is conjugated, and a non-conjugated double bond:

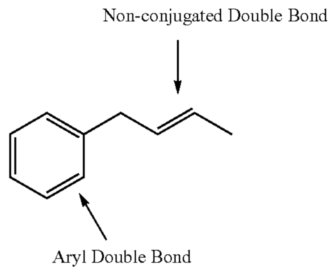

Each alkoxy (e.g., $C_1$-$C_6$ alkoxy), alkyl (e.g., $C_1$-$C_6$ alkyl), aryl (e.g., $C_4$-$C_{14}$ aryl), and the like disclosed herein, includes all substituted, unsubstituted, branched, and linear analogs or derivatives thereof, in each instance having the indicated number of carbon atoms. Examples of alkyl groups include, but are not limited to, methyl, ethyl, propyl, isopropyl, n-butyl, t-butyl, isobutyl, pentyl, hexyl, isohexyl, cyclopropyl, cyclobutyl, cyclopentyl, and cyclohexyl. Additional examples of alkyl moieties have linear, branched and/or cyclic portions. Examples of alkoxy compounds include any of the foregoing alkyl groups that are covalently bonded to an oxygen atom. Examples of aryl moieties include, but are not limited to, anthracenyl, azulenyl, biphenyl, fluorenyl, indan, naphthyl, phenyl, 1,2,3,4-tetrahydro-naphthalene, and the like, including substituted derivatives thereof. Substituted derivatives of aromatic compounds include, but are not limited to, tolyl, xylyl, mesityl, and the like, including any heteroatom substituted derivative thereof.

Each aryl group (e.g., $C_4$-$C_{14}$ aryl group) of the compounds provided herein may independently include (i) a single "R" substituent (for example, one of $R^2$, $R^3$, $R^5$, $R^6$, $R^8$, or $R^9$), or (ii) at least two "R" substituents on adjacent carbon atoms (for example, $R^2$ and $R^3$, wherein $R^2$ and $R^3$ are covalently bonded to each other; $R^3$ and $R^4$, wherein $R^3$ and $R^4$ are covalently bonded to each other; etc.). Therefore, for example, in Formula (I), an unsubstituted $C_6$ aryl group (i.e., a phenyl) may be selected for each of $R^3$ and $R^4$ (Structure (a)), or an unsubstituted $C_4$ aryl group may be selected jointly for $R^3$ and $R^4$, thereby resulting in a 6-membered aryl ring that includes the carbon atom to which $R^3$ is covalently bonded, the carbon atom to which $R^4$ is covalently bonded, $R^3$, and $R^4$, wherein $R^3$ and $R^4$ are covalently bonded to each other (Structure (b)):

Structure (a)

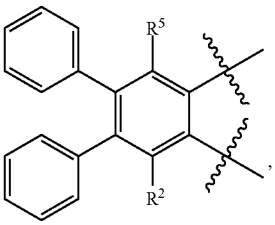

,

Structure (b)

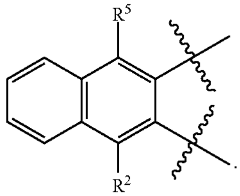

.

Each alkoxy (e.g., $C_1$-$C_6$ alkoxy) and/or alkyl (e.g., $C_1$-$C_6$ alkyl), of the compounds provided herein may independently include (i) a single "R" substituent (for example, one of R', R'', $R^2$, $R^3$, $R^5$, $R^6$, $R^8$, or $R^9$), or (ii) at least two "R" substituents on adjacent carbon atoms (for example, $R^2$ and $R^3$, wherein $R^2$ and $R^3$ are covalently bonded to each other; $R^3$ and $R^4$, wherein $R^3$ and $R^4$ are covalently bonded to each other; R' and $R^3$, wherein R' and $R^3$ are covalently bonded to each other, etc.). Therefore, for example, in Formula (I), an unsubstituted $C_6$ alkyl group (i.e., a hexyl) may be selected for each of $R^3$ and $R^4$ (Structure (a)), or an unsubstituted $C_4$ alkyl group may be selected jointly for $R^3$ and $R^4$, thereby resulting in a 6-membered ring that includes the carbon atom to which $R^3$ is covalently bonded, the carbon atom to which $R^4$ is covalently bonded, $R^3$, and $R^4$, wherein $R^3$ and $R^4$ are covalently bonded to each other (Structure (b)):

Structure (a)

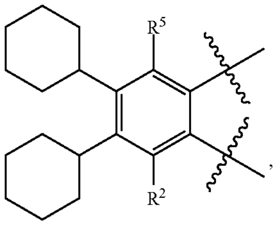

,

Structure (b)

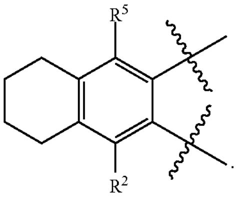

.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkyl (e.g., methyl, ethyl, propyl, t-butyl), alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., $—CCl_3$, $—CF_3$, $—C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether), urea (—NHCONH-alkyl-), or a combination thereof. When an "R" group (e.g., $R^1$) is substituted, the carbon atoms in the substituents are included in the total count of carbon atoms in the "R" group. For example, if $R^1$ is selected from a $C_1$-$C_6$ alkyl, and the $C_1$-$C_6$ alkyl is a propyl group substituted with a dimethylamine substituent, then $R^1$ is considered, in this example, to be a $C_5$ alkyl because there are 3 carbon atoms in the propyl group, and 2 carbon atoms in the dimethylamine substituent.

When a compound or isomer of Formula (I) includes a stereocenter, the compounds or isomers of Formula (I) include both of the (R) and (S) enantiomers. Therefore, the compounds of isomers of Formula (I) may include and read on (i) the (R) enantiomer of a hypothetical compound X, (ii) the (S) enantiomer of compound X, or (iii) a mixture of the (R) and (S) enantiomers of compound X, including a racemic mixture.

In some embodiments, the compound is a compound or isomer of Formula (I), wherein $R^4$ is hydroxyl, $R^7$ is oxygen, and the compound has a structure according to Formula (IA):

Formula (IA)

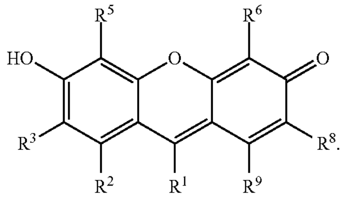

In some embodiments, the compound is a compound of Formula (IA), wherein $R^2$, $R^3$, $R^5$, $R^6$, $R^8$, and $R^9$ are hydrogen, and the compound has a structure according to Formula (IB):

Formula (IB)

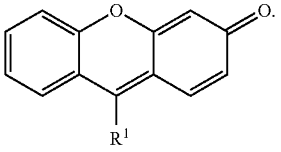

In some embodiments, the compound is a compound or isomer of Formula (I), wherein $R^4$ is a first —NR'R", $R^7$ is a second —NR'R", wherein the first and second —NR'R" are the same or different, and the compound has a structure according to Formula (IC). Compounds of Formula (IC) or other compounds described herein that include a positively charged atom or moiety may be associated with any known anion. In some embodiments, the anion is an inorganic anion such as a halide, e.g., $Cl^-$.

Formula (IC)

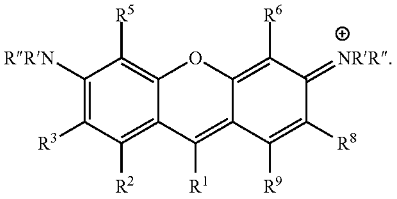

In some embodiments, the compound is a compound of Formula (IC), wherein $R^2$, $R^3$, $R^5$, $R^6$, $R^8$, and $R^9$ are hydrogen, and the compound has a structure according to Formula (ID):

Formula (ID)

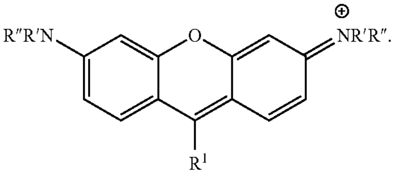

In some embodiments, the compound is a compound of Formula (IC), wherein each R' and each R" are hydrogen, and the compound has a structure according to Formula (IE):

Formula (IE)

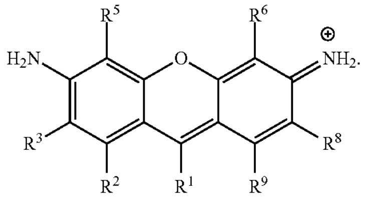

In some embodiments, the compound is a compound of Formula (IE), wherein $R^2$, $R^3$, $R^5$, $R^6$, $R^8$, and $R^9$ are hydrogen, and the compound has a structure according to Formula (IF):

Formula (IF)

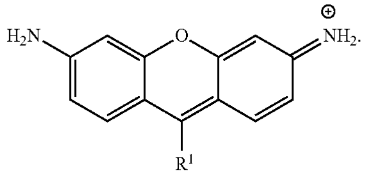

In some embodiments, the compound is a compound of Formula (IC), wherein each R' and each R" are ethyl, and the compound has a structure according to Formula (IG):

Formula (IG)

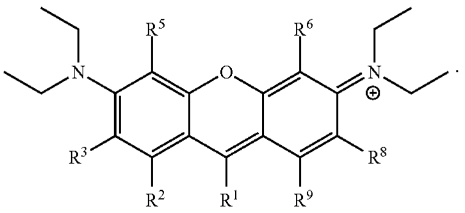

In some embodiments, the compound is a compound of Formula (IG), wherein $R^2$, $R^3$, $R^5$, $R^6$, $R^8$, and $R^9$ are hydrogen, and the compound has a structure according to Formula (IH):

Formula (IH)

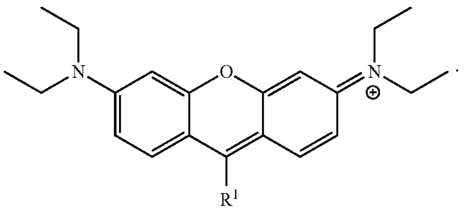

In some embodiments, the compound is a compound or isomer of any one of Formula (I), Formula (IA), Formula (IB), Formula (IC), Formula (ID), Formula (IE), Formula (IF), Formula (IG), or Formula (IH), wherein $R^1$ is selected from one of the following moieties, which may be unsubstituted or substituted as described herein—

| $R^1$ | |
|---|---|
| $C_1$-$C_{10}$ hydrocarbyl | $C_1$-$C_{10}$ hydrocarbyl substituted with a carboxylic acid moiety and/or sulfonic acid moiety |
| $C_1$-$C_9$ hydrocarbyl | $C_1$-$C_9$ hydrocarbyl substituted with a carboxylic acid moiety and/or sulfonic acid moiety |
| $C_1$-$C_8$ hydrocarbyl | $C_1$-$C_8$ hydrocarbyl substituted with a carboxylic acid moiety and/or sulfonic acid moiety |
| $C_1$-$C_7$ hydrocarbyl | $C_1$-$C_7$ hydrocarbyl substituted with a carboxylic acid moiety and/or sulfonic acid moiety |
| $C_1$-$C_6$ hydrocarbyl | $C_1$-$C_6$ hydrocarbyl substituted with a carboxylic acid moiety and/or sulfonic acid moiety |
| $C_1$-$C_5$ hydrocarbyl | $C_1$-$C_5$ hydrocarbyl substituted with a carboxylic acid moiety and/or sulfonic acid moiety |
| $C_1$-$C_4$ hydrocarbyl | $C_1$-$C_4$ hydrocarbyl substituted with ac arboxylic acid moiety and/or sulfonic acid moiety |
| $C_1$-$C_3$ hydrocarbyl | $C_1$-$C_3$ hydrocarbyl substituted with a carboxylic acid moiety and/or sulfonic acid moiety |
| $C_2$-$C_3$ hydrocarbyl | $C_2$-$C_3$ hydrocarbyl substituted with a carboxylic acid moiety and/or sulfonic acid moiety |
| $—(CH_2)_nCH_3$, wherein n is 1-5 | $—(CH_2)_nCOOH$, wherein n is 1-5 |
| $—(CH_2)_2CH_3$ | $—(CH_2)_2COOH$ |
| $—C_6H_5$ | 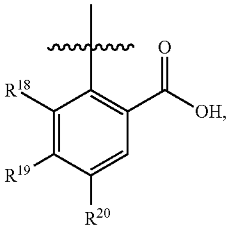 wherein $R^{18}$, $R^{19}$, and $R^{20}$ are independently selected from the group consisting of hydrogen, hydroxyl, $C_1$-$C_6$ alkoxy, |

-continued

| $R^1$ | |
|---|---|
| | $—N(R')(R')$, $C_1$-$C_6$ alkyl, and $C_4$-$C_{14}$ aryl |
| | 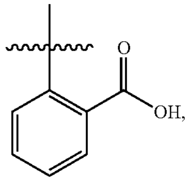 [SMILES: *c1ccccc1C(=O)O] which is referred to herein as "-ortho-$(C_6H_4)COOH$" |

In some embodiments, the compound is a compound or isomer of Formula (I), wherein $R^2$, $R^3$, $R^5$, $R^6$, $R^8$, and $R^9$ are hydrogen, $R^4$ is hydroxyl, $R^7$ is oxygen, $R^1$ is $—(CH_2)_2COOH$, and the first monomer is 3-(6-hydroxy-3-oxo-3H-xanthen-9-yl)propanoic acid, a salt, a hydrate, a salt hydrate, a stereoisomer, a dehydrate, a tautomer, or a derivative thereof—

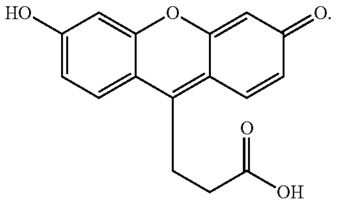 [SMILES: O=C(O)CCc1c2ccc(=O)cc-2oc2cc(O)ccc12]

As explained herein, the compounds or isomers of Formula (I) also include the tautomers thereof. For example, a tautomer of 3-(6-hydroxy-3-oxo-3H-xanthen-9-yl)propanoic acid may include 3',6'-dihydroxy-3,4-dihydro-5H-spiro[furan-2,9'-xanthen]-5-one, as depicted in the following scheme:

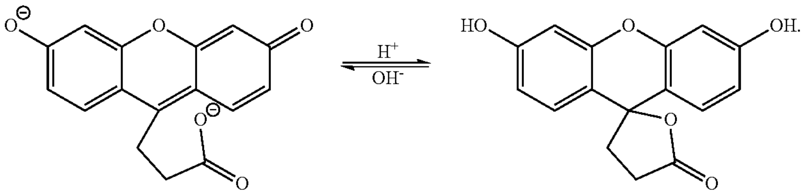

As explained herein, the fluorescence emission of the foregoing tautomers may differ; therefore, the fluorescence emission of the compounds or isomers herein may depend, at least in part, on pH. Selection of a pH may permit fluorescence emission to be tuned.

In some embodiments, the compound is a compound or isomer of Formula (I), wherein $R^2$, $R^3$, $R^5$, $R^6$, $R^8$, and $R^9$ are hydrogen, $R^4$ is hydroxyl, $R^7$ is oxygen, $R^1$ is -ortho-$(C_6H_4)COOH$, and the first monomer is 2-(6-hydroxy-3-oxo-3H-xanthen-9-yl)benzoic acid, a salt, a hydrate, a salt hydrate, a stereoisomer, a dehydrate, a tautomer, or a derivative thereof—

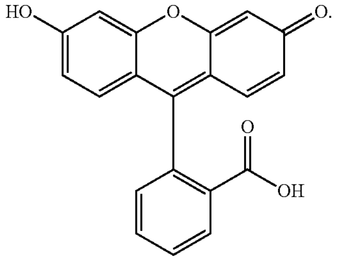 [SMILES: O=C(O)c1ccccc1-c1c2ccc(=O)cc-2oc2cc(O)ccc12]

In some embodiments, the compound is a compound or isomer of Formula (I), wherein $R^1$ is -ortho-$(C_6H_4)COOH$, $R^2$, $R^3$, $R^5$, $R^6$, $R^8$, and $R^9$ are hydrogen, $R^4$ and $R^7$ are —NR'R'', wherein R' and R'' are ethyl, and the first monomer is rhodamine B, a salt, a hydrate, a salt hydrate, a stereoisomer, a dehydrate, a tautomer, or a derivative thereof—

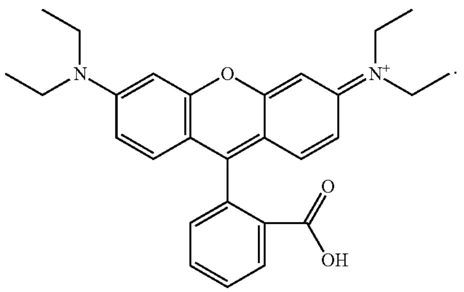 [SMILES: CCN(CC)c1ccc2c(-c3ccccc3C(=O)O)c3ccc(=[N+](CC)CC)cc-3oc2c1]

Polymer Compositions

Polymer compositions, including scale-inhibiting polymer compositions, are provided herein. The polymer compositions include a copolymer, which includes a first monomer that is a tagging monomer, and at least one second monomer that is a scale-inhibiting monomer.

In some embodiments, the first monomer is selected from a compound or isomer of Formula (I), which, again, includes salts, hydrates, salt hydrates, stereoisomers, dehydrates, tautomers, or derivatives of the compounds or isomers of Formulas (I). In some embodiments, the at least one second monomer includes at least one polymerizable double bond or at least one polymerizable triple bond.

In some embodiments, the copolymers are obtainable by free radical polymerization of two or more types of monomer (including 3, 4, or more different monomers) without restriction on the number of monomer units that are incorporated into the product, provided that at least one of the monomers is a first monomer (i.e., a tagging monomer) and at least one of the monomers is a second monomer (i.e., a scale-inhibiting monomer). In some embodiments, the copolymers include two or more second monomers (i.e., scale-inhibiting units) and one or more first monomers (i.e., tagging units) as described herein.

As used herein, the terms "polymer," "polymers," "polymeric," and the like are used in their ordinary sense as understood by one skilled in the art, and thus may be used herein to refer to or describe a large molecule (or group of such molecules) that contains recurring units (i.e., monomers), including, but not limited to, oligomers, comb polymers, branched polymers, linear polymers, crosslinked polymers, star polymers, etc. Polymers may be formed in various ways, including by polymerizing monomers and/or by chemically modifying one or more recurring units of a precursor polymer. A polymer may be a "copolymer" that includes two or more different recurring units (i.e., monomers) formed by, e.g., copolymerizing two or more different monomers (e.g., 2, 3, 4, 5, 6 or more monomers), and/or by chemically modifying one or more recurring units of a precursor polymer.

The polymers, including copolymers, provided herein are defined in terms of the monomer(s) that form the structures of the polymers. Although, in the interest of clarity, monomers are depicted in isolated, unpolymerized form herein, a person skilled in the art will understand the structural differences between the monomers in unpolymerized and polymerized forms (see, e.g., the possible polymer structure depicted at Example 2).

The term "anti-scalant", the phrases "scale inhibition", "scale inhibitor" or "scale-inhibiting", and the like generally refer to materials (e.g., monomers, polymer compositions, etc.) that may be applied (e.g., at substoichiometric levels) to interfere with crystal nucleation, growth, agglomeration, or a combination thereof. As used herein, the terms "anti-scalant", the phrases "anti-scale agent" and "scale inhibitor", and the like are used in their ordinary sense as understood by one skilled in the art, and thus may be used herein to refer to or describe chemical compounds or compositions, such as polymer compositions, containing such compounds, where the compounds, when added to an system, reduce or inhibit the amount of scale and/or rate of formation of scale in the system, as compared to a system that does not contain the added chemical compound or composition. In this context, the term "scale" or the phrase "mineral scale" refer to insoluble substances, such as insoluble salts, that may have a tendency to form in aqueous systems, such as boiler water, cooling water, seawater (e.g., in oil platform applications), brackish water, oilfield water, municipal treatment plant water, paper mill water, mining water, industrial treatment plant water, etc.

The phrases "treatment of scale", "treated for scale", "preventing or reducing scale formation", and the like will be understood by those skilled in the art to have a broad and customary meaning that includes using the scale-inhibiting polymer compositions herein to (i) reduce an amount of scale, (ii) inhibit an amount of scale, (iii) reduce a rate of formation of scale, or (iv) a combination thereof in various systems, including aqueous systems, as compared to comparable systems that do not contain the anti-scale polymer composition.

i. First Monomer

The first monomer of the polymer compositions may include a compound or isomer of Formula (I), which, again, may include salts, hydrates, salt hydrates, stereoisomers, dehydrates, tautomers, or derivatives of the compounds or isomers of Formula (I). Therefore, the first monomer, for example, may include a salt or salt hydrate of a compound or isomer of Formula (I), such as a hydrochloride, dihydrochloride, sulfate, bisulfate, or gluconate salt, or hydrate thereof. As a further example, the first monomer may include a derivative of a compound or isomer of Formula (I), such as a derivative formed from the addition of acid or base and heat to the compound or isomer of Formula (I).

ii. Second Monomer

The at least one second monomer of the polymer compositions provided herein may include any monomer that (i) includes a polymerizable moiety, such as a double bond or a triple bond, and (ii) is a scale inhibitor before and after polymerization, or after polymerization.

In some embodiments, the at least one second monomer is selected from the group consisting of allylsulfonate salts, for example sodium allylsulfonate; acrylic acid; vinyl sulfonic acid; vinyl sulfonate salts; vinyl phosphoric acid; vinyl phosphonate salts; vinylidene diphosphonic acid or salts thereof; methacrylic acid; vinyl acetate; vinyl alcohol; vinyl chloride; unsaturated mono- or di-carboxylic acids or anhydrides, such as maleic anhydride, maleic acid, fumaric acid, itaconic acid, aconitic acid, mesaconic acid, citraconic acid, crotonic acid, isocrontonic acid, angelic acid, and tiglic acid; vinyl chloride; styrene-p-sulfonic acid, or styrene sulfonates salts; acrylamido-2-methylpropanesulfonic acid (AMPS); hydroxyphosphonoacetic acid (HPA); hypophosphorus acids; acrylamides; propargyl alcohol having formula $HC\equiv C-CH_2-OH$; butyr-1,4-diol, and mixtures thereof. In some embodiments, two or more types of scale-inhibiting monomer are used as the at least one second monomer; for example, (i) sodium allylsulfonate and maleic acid, (ii) sodium allylsulfonate and maleic anhydride, (iii) sodium allylsulfonate and acrylic acid, or (iv) sodium allylsulfonate, acrylic acid, and at least one of maleic acid or maleic anhydride. In some embodiments, the at least one second monomer includes at least one of maleic acid, maleic anhydride, or acrylic acid.

The polymer compositions provided herein generally may include any amount of at least one first monomer and any amount of at least one second monomer. In some embodiments, the first monomer is present in the copolymer at an amount of about 0.01% to about 10%, by weight, based on the weight of the copolymer. In some embodiments, the first monomer is present in the copolymer at an amount of about 0.01% to about 5%, by weight, based on the weight of the copolymer. In some embodiments, the first monomer is present in the copolymer at an amount of about 0.01% to about 2%, by weight, based on the weight of the copolymer. In some embodiments, the first monomer is present in the copolymer at an amount of about 0.01% to about 1.5%, by weight, based on the weight of the copolymer. In some embodiments, the first monomer is present in the copolymer at an amount of about 0.01% to about 1%, by weight, based on the weight of the copolymer. In some embodiments, the first monomer is present in the copolymer at an amount of about 0.01% to about 0.75%, by weight, based on the weight of the copolymer. In some embodiments, the first monomer is present in the copolymer at an amount of about 0.01% to about 0.5%, by weight, based on the weight of the copolymer. In some embodiments, the first monomer is present in the copolymer at an amount of about 0.01% to about 30%, about 0.01% to about 20%, about 0.01% to about 15%, about 0.01% to about 10%; about 0.01% to about 8%; about 0.01% to about 7%; about 0.01% to about 5%; about 0.01% to about 3%, or about 0.01% to about 2%, by weight, based on weight of the copolymer.

In some embodiments, the copolymer of a polymer composition has a weight average molecular weight ($M_w$) of about 500 Daltons to about 20,000 Daltons, about 1,200 Daltons to about 15,000 Daltons, about 2,000 Daltons to about 10,000 Daltons, about 2,000 Daltons to about 8,000 Daltons, about 2,000 Daltons to about 6,000 Daltons, about 2,000 Daltons to about 4,000 Daltons, or about 2,000 Daltons to about 3,000 Daltons.

In some embodiments, the polymer compositions may include one or more monomers, groups, or units, as necessary or desired, in addition to the first monomer and at least one second monomer. For example, the polymers may include one or more other groups resulting from a polymerization initiator, end-capping groups, or a combination thereof. In some embodiments, the end capping groups are derived from initiator compounds used in the polymerization of monomers.

The thermal stability of the polymer compositions may be evaluated by heating the polymer in a liquid, for example water or brine, to a temperature, for example, of about 80° C., about 90° C., about 100° C., about 110° C., about 120° ° C., or about 130° C., and keeping polymer composition in the liquid at that temperature for a period of time, for example, about one week.

In some embodiments, the polymer compositions, including the copolymers provided herein, have a thermal stability such that when a polymer composition is kept at a temperature of about 80° C. in water or brine for about one week, there is less than about a 15%, about a 10%, about a 5%, about a 4%, or about a 3% decrease in emission intensity. In some embodiments, the polymer compositions, including the copolymers provided herein, have a thermal stability such that when a polymer composition is kept at a temperature of about 130° C. in water or brine for about one week, there is less than about a 15%, about a 10%, about a 5%, about a 4%, or about a 3% decrease in emission intensity. In some embodiments, the water is at a pH of about 7 to about 8. In some embodiments, the brine is natural brine or synthetic brine. In some embodiments, the polymer compositions have a thermal stability such that when a polymer composition is kept at a temperature of about 80° C. in water for about one week, there is less than about a 10%, about a 5%, about a 4%, or about a 3% decrease in emission intensity. In some embodiments, the polymer compositions have a thermal stability such that when a polymer composition is kept at a temperature of about 130° C. in water for about one week, there is less than about a 15%, about a 10% or about a 5% decrease in emission intensity. In some embodiments, the polymer compositions have a thermal stability such that when a polymer composition is kept at a temperature of about 130° C. in water at about pH 8 for about one week, there is less than about a 15%, about a 13%, or about a 10% decrease in emission intensity. In some embodiments, the polymer compositions have a thermal stability such that when a polymer composition is kept at a temperature of about 130° C. in brine for about one week, there is less than about a 20%, about a 15% or about a 10% decrease in emission intensity.

A copolymer, as provided herein, may be present in the polymer compositions at an effective scale-inhibiting amount. As used herein, the phrase "effective scale-inhibiting amount" refers to an amount of a scale-inhibiting copolymer that is effective to provide suitable scale inhibition, removal, reduction, or a combination thereof. In some embodiments, the polymer compositions include an effective scale-inhibiting amount of a copolymer that includes a first monomer and at least one second monomer as described herein. Exemplary scale-inhibiting polymer compositions may, for example, include from about 5% to about 95%, by weight, of a scale-inhibiting copolymer that includes a first monomer and at least one second monomer, based on the total weight of the scale-inhibiting polymer composition.

The polymer composition may optionally include one or more additional ingredients, as necessary or desired, such as those described herein, which include water, salts, oils, surfactants, pH adjusting agents (such as acids, bases and buffers), colorants, flow modifiers, other water treatment agents, etc. In some embodiments, the polymer composition consists essentially of a copolymer that includes a first monomer and at least one second monomer, as described herein. When the polymer composition consists essentially of a copolymer that includes a first monomer and at least one second monomer, the polymer composition may include one or more of the foregoing “additional ingredients” and the following “[e]xemplary fluids”, because the “additional ingredients” and “[e]xemplary fluids” are non-limiting examples of components that do not materially affect the basic and novel characteristic(s) of the polymer compositions.

In some embodiments, the polymer compositions include (i) a copolymer of a first monomer and at least one second monomer, and (ii) a fluid. Exemplary fluids include those that may be in or intended for industrial water systems or process systems, such as boilers, cooling systems, cooling towers, desalination plants, geothermal power production, irrigation systems, mineral ore extraction systems, paper pulping or manufacturing systems, membrane systems, etc. Other exemplary fluids include fluids for use in the oil industry, such as those for use in the treatment of water injection systems, subsea flow lines, topside production equipment and “down-hole” to control scaling in and around the production well-bore.

In some embodiments, the polymer compositions include an aqueous composition or a water-based fluid, for example a seawater-based fluid. Other fluids, however, are envisioned. In some embodiments, the polymer compositions include a glycol or glycol ether based solvent.

In some embodiments, the polymer compositions include a copolymer of a first monomer and at least one second monomer, as described herein, and, optionally, one or more additional polymers, such as one or more additional scale-inhibiting polymers. The one or more additional polymers may include a tagging agent, and the fluorescence emission of the tagging agent may differ from the fluorescence emission of the first monomer of the copolymer.

In some embodiments, the polymer composition includes one or more copolymers, as described herein, in combination with one or more additional ingredients, such as anionic surfactants (e.g., $C_{10-20}$ alkyl benzene sulfonates, $C_{10-20}$ olefin sulfonates, $C_{10-20}$ alkyl sulfates, $C_{10-20}$ alkyl 1 to 25 mole ether sulfates, $C_{10-20}$ paraffin sulfonates, $C_{10-20}$ soaps, $C_{10-20}$ alkyl phenol sulfates, sulfosuccinates, sulfosuccinamates, lignin sulfonates, fatty ester sulfonates, $C_{10-20}$ alkyl phenyl ether sulfates, $C_{10-20}$ alkyl ethanolamide sulfates, $C_{10-20}$ alpha sulfo fatty acid salts, $C_{10-20}$ acyl sarcosinates, isethionates, $C_{10-20}$ acyl taurides, $C_{10-20}$ alkyl hydrogen phosphates), non-ionic surfactants (e.g. ethoxylated and/or propoxy lated $C_{10-20}$ alcohols, ethoxylated and/or propoxylated $C_{10-20}$ carboxylic acids, alkanolamides, amine oxides, and/or $C_{10-20}$ acyl sorbitan and/or glyceryl ethoxylates), amphoteric surfactants (e.g. betaines, sulfobetaines, and/or quaterised imidazolines), and/or cationic surfactants (e.g. benzalkonium salts, $C_{10-20}$ alkyl trimethyl ammonium salts, and/or $C_{10-20}$ alkyl trimethyl); sequestrants; chelating agents; corrosion inhibitors (e.g., imidazoline and quaterantry ammonium salts); and/or other threshold agents (e.g. polymers such as aminometholine phosphonate polymers, polyacrylic acid, or non polymeric agents such as sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid and its salts); tolyltriazole and mixtures of nitrate, benzoate, HHP and/or PTCB); hydrate inhibitors (e.g., methanol); cinetic inhibitors such as anti-agglomeration agents; biocides (e.g. tetrakis (hydroxymethyl) phosphonium salts, formaldehyde, glutaraldehyde, DENPA, bromopol isothiazoronal); oxidising biocides and/or bleaches (e.g. chlorine, chlorine dioxide, hydrogen peroxide, sodium perborate); foam controlling agents, such as silicone antifoams; oxygen scavengers such as hydrazines and/or hydroxylamines; pH controlling and/or buffering agents, such as amines, borates, citrates and/or acetates; chromium salts; zinc salts; asphaltene inhibitors; wax inhibitors; demulsifiers; other scale inhibitors; and/or other water treatment agents such as polymeric dispersants and coagulants including polymaleic, polyacrylic and polyvinylsulfonic acids and their salts, starches and/or carboxy methyl cellulose, and/or molybdates.

In some embodiments, the polymer composition includes two or more copolymers. When two or more copolymers are present, each copolymer may include a different first monomer, and each of the different first monomers may exhibit a different fluorescence emission. For example, a polymer composition may include (i) a first copolymer including a first monomer, such as resorcinmalein, which has a fluorescence emission maximum of about 500 to about 520 nm, (ii) a second copolymer including a first monomer, such as one based on diethylaminophenol, which has a fluorescence emission maximum of about 550 nm to about 590 nm, (iii) a third copolymer including a first monomer, such as naphthomalein, which has a fluorescence emission maximum of about 640 nm to about 680 nm, or (iv) a combination thereof. Such a polymer composition also may include an additional copolymer including a first monomer, such as hydroxyjulolidine, which has a fluorescence emission maximum of about 570 nm to about 600 nm. The differences in fluorescence emission maximum may permit the methods described herein to be used to determine an amount of each copolymer present in a fluid or system, the differences between the amounts of each copolymer in a fluid or system, or a combination thereof.

In some embodiments, the polymer compositions include about 5% to about 95%, by weight, of a copolymer of a first monomer and at least one second monomer, as described herein, and about 5% to about 90%, by weight, of one or more of any of the additional ingredients described herein, based on the total weight of a polymer composition.

A copolymer of at least one first monomer and at least one second monomer may be combined with water using any suitable method. For example, a copolymer may be dissolved, suspended, dispersed, or emulsified in water. The amount of water in an aqueous polymer composition may vary, as necessary or desired. For example, an aqueous polymer composition may include about 20% to about 80%, by weight, of a copolymer of a first monomer and a second monomer, as described herein, based on the total weight of the aqueous polymer composition.

In some embodiments, the pH of a polymer composition may be such that the acidic functionalities of a copolymer, as described herein, are neutralized. For example, the composition may be neutralized by adjusting the pH of the composition to a pH in a range of about 2 to about 13.

Methods of Synthesis

The compounds or isomers of Formula (I) may be synthesized with any technique, including those provided herein.

In some embodiments, the compounds or isomers of Formula (I) are formed via a condensation reaction. The condensation reaction may include contacting an aryl alcohol, a condensation catalyst, and a compound according to Formula (A) or Formula (B) to form the condensation product. The condensation product may include a compound or isomer of Formula (I), which, as explained herein, includes the salts, hydrates, salt hydrates, stereoisomers, dehydrates, tautomers, and derivatives of the compounds or isomers of Formula (I).

The compounds according to Formula (A) and Formula (B) have the following structure:

Formula (A)

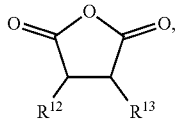

Formula (B)

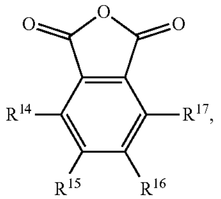

wherein $R^{12}$, $R^{13}$, $R^{14}$, $R^{15}$, $R^{16}$, and $R^{17}$ are independently selected from the group consisting of hydrogen, hydroxyl, and $C_1$-$C_6$ alkyl.

In some embodiments, $R^{12}$ and $R^{13}$ are hydrogen, and the compound of Formula (A) is dihydrofuran-2,5-dione, i.e., succinic anhydride:

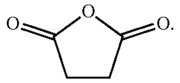

In some embodiments, $R^{14}$, $R^{15}$, $R^{16}$, and $R^{17}$ are hydrogen, and the compound of Formula (B) is isobenzofuran-1,3-dione:

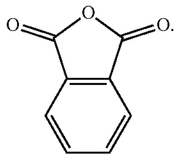 [SMILES: O=C1OC(=O)c2ccccc21]

As used herein, the phrase "aryl alcohol" generally refers to a compound that includes (i) an aryl moiety, and (ii) at least one hydroxyl moiety. In some embodiments, the aryl alcohol is a phenol. In some embodiments, the aryl alcohol includes (i) an aryl moiety, and (ii) two hydroxyl moieties. In some embodiments, the aryl alcohol is resorcinol. In some embodiments, the aryl alcohol is 1,6-dihydroxynaphthalene. The aryl alcohol, however, may include any compound that is capable of forming a compound or isomer of Formula (I).

The contacting of the aryl alcohol, the condensation catalyst, and the compound of Formula (A) or Formula (B) may occur at any temperature and/or pressure that is effective to form the condensation product. In some embodiments, the contacting of the aryl alcohol, the condensation catalyst, and the compound of Formula (A) or Formula (B) occurs at a temperature of about 25° C. to about 200° C., about 50° C. to about 150° C., about 75° C. to about 150° C., about 100° C. to about 150° C., or about 100° C. to about 125° C. In some embodiments, the contacting of the aryl alcohol, the condensation catalyst, and the compound of Formula (A) or Formula (B) occurs at ambient pressure, and a temperature of about 25° C. to about 200° C., about 50° C. to about 150° C., about 75° C. to about 150° C., about 100° C. to about 150° C., or about 100° C. to about 125° C.

The condensation catalyst may include any catalyst capable of effecting the condensation of the aryl alcohol and the compound of Formula (A) or Formula (B). In some embodiments, the condensation catalyst is a Lewis acid. Non-limiting examples of Lewis acids include $ZnCl_2$, $FeCl_3$, $AlCl_3$, and $BCl_3$. In some embodiments, the condensation catalyst is a sulfonic acid. The sulfonic acid may include an $C_1$-$C_6$ alkyl sulfonic acid, a $C_5$-$C_{14}$ aryl sulfonic acid, or a combination thereof. In some embodiments, the $C_1$-$C_6$ alkyl sulfonic acid is methanesulfonic acid ($MeSO_3H$). In some embodiments, the $C_5$-$C_{14}$ aryl sulfonic acid is p-toluenesulfonic acid.

Also provided herein are methods of polymerizing a compound or isomer of Formula (I). In some embodiments, the methods include contacting a compound or isomer of Formula (I), (e.g., a condensation product of the foregoing methods) with at least one second monomer to form a copolymer, wherein the at least one second monomer includes a polymerizable double bond or triple bond. The at least one second monomer may be contacted with an amount of the condensation product effective to produce a copolymer that includes a desirable amount of the condensation product as described herein, such as about 0.01% to about 5%, or about 0.01% to about 2%, by weight, based on the weight of the copolymer.

The at least one second monomer generally may include any monomer that is polymerizable due to the presence of a polymerizable double bond or triple bond. The phrases "polymerizable double bond", "polymerizable triple bond", and the like refer to bonds that may react with a functional group of at least one other monomer (e.g., under conditions described herein) to form a polymer. The at least one second monomer may be a scale-inhibitor alone and/or when polymerized. In some embodiments, the at least one second monomer includes sodium allyl sulfonate and at least one of maleic acid, maleic anhydride, or acrylic acid. In some embodiments, the at least one second monomer includes at least one of maleic acid, maleic anhydride, or acrylic acid. In some embodiments, the at least one second monomer includes a compound of Formula (II)—

Formula (II)

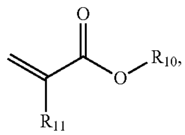

wherein $R^{10}$ and $R^{11}$ are independently selected from the group consisting of hydrogen and alkyl (e.g., a $C_1$-$C_6$ alkyl). In some embodiments, $R^{10}$ and $R^{11}$ are hydrogen. In some embodiments, $R^{11}$ is an unsubstituted $C_1$ alkyl, and $R^{10}$ is hydrogen.

The polymer compositions provided herein generally may be prepared by any polymerization method. For example, a free-radical polymerization method may be employed. Other exemplary methods include aqueous bulk/dispersion polymerization, solution polymerization, or emulsion polymerization. In some embodiments, the polymerization process is a solution polymerization, wherein water is charged to a reaction vessel fitted with a mechanical stirrer and water condenser, and heated to a temperature within a range of about 45° C. to about 150° C., or about 45° C. to about 110° C. One or more polymerization initiators may be added to the reactor. The choice of initiator may inform the temperature at which the reaction is performed. A first monomer may be added to the reactor, added to a monomer feed or fed separately. A monomer feed(s), soluble initiator feed, and optionally a chain transfer reagent feed may be added to a vessel at a predetermined time or over time.

In some embodiments, the polymerization of monomers, including at least one first monomer and at least one second monomer, is achieved in the presence of one or more polymerization initiators including, but not limited to, inorganic peroxides, for example ammonium persulfate (APS), hydroxymethanesulfinic acid monosodium salt dehydrate, potassium persulfate, and sodium persulfate; organic peroxides, for example tert-butyl hydroperoxide (TBHP), tert-butyl peracetate, cumene hydroperoxide, 2,5-Di(tert-butylperoxy)-2,5-dimethyl-3-hexyne, dicumyl peroxide, 2,5-bis(tert-butylperoxy)-2,5-dimethylhexane, 2,4-pentanedione peroxide, 1,1-bis(tert-butylperoxy)-3,3,5-trimethylcyclohexane, 1,1-bis(tert-butylperoxy)cyclohexane, 1,1-bis(tert-amylperoxy)cyclohexane, benzoyl peroxide, 2-butanone peroxide, tert-butyl peroxide, lauroyl peroxide, tert-butyl peroxy benzoate, and tert-butylperoxy 2-ethylhexyl carbonate; azo compounds, for example azobisisobutyronitrile (AIBN), 4,4'-azobis(4-cyanovaleric acid), 1,1'-azobis(cyclohexanecarbonitrile), 2,2'-azobis(2-methylpropionamidine) dihydrochloride, and 2,2'-azobis(2-methylpropionitrile); tetrakis(hydroxy methyl)phosphonium sulfate (THPS); cerium ammonium nitrate; perchlorates; triphenylphosphine; and the like, and compositions or mixtures including one or more of these initiators. In some embodiments, the initiator is selected from the group consisting of ammonium persulfate, tert-butyl hydroperoxide, and 4,4'-azobis(4-cyanovaleric acid).

Polymerization initiators generally may be used at an amount of about 0.01% to about 10%, by weight, based on the total weight of the monomers. Polymerization initiators may be used in conjunction with heat to initiate polymerization of monomers. In some embodiments, two or more initiators are used; for example, an inorganic peroxide and an organic peroxide. In some embodiments, ammonium persulfate (APS) and an organic peroxide are used to initiate polymerization. The initiator or initiators used to achieve polymerization may affect the physical properties of the resulting polymer. The initiator or initiators may be added to a polymerization reaction mixture, for example, at the start of the reaction, at various times during the polymerization, and/or gradually over time, e.g., over several minutes or hours. If two or more initiators are used, then the initiators may be dosed simultaneously or sequentially during polymerization. In some embodiments, one initiator is dosed at the start of polymerization, at various times during polymerization, and/or gradually over time, and a different initiator is used at later stages the polymerization.

Methods of Preventing or Reducing Scale Formation

Methods for preventing or reducing scale formation also are provided. In some embodiments, the methods include providing a system that includes a fluid in circulation, wherein the fluid includes a scale-inhibiting polymer composition as described herein; measuring with an analytical technique an amount of the first monomer in the system or the fluid to determine an amount of the polymer composition in the system or the fluid, wherein the measuring is performed periodically or continuously; and optionally (i) adding an additional amount of the polymer composition to the system or the fluid if the amount of the polymer composition in the system or the fluid is less than a predetermined value, or (ii) removing a portion of the polymer composition from the system or the fluid if the amount of the polymer composition in the system or the fluid is greater than the predetermined value.

As used herein, the phrase "amount of the first monomer", the phrase "amount of the polymer composition", and the like refer to and include (i) an actual numerical amount (e.g., X grams) of the first monomer or the polymer composition, respectively, in a fluid or system, or (ii) a concentration (e.g., X ppm) of the first monomer or polymer composition, respectively, in a fluid or system.

In some embodiments, the methods include (a) adding to a system or fluid a predetermined amount of a scale-inhibiting polymer composition as described herein; (b) periodically or continuously measuring the amount of tagging units (i.e., first monomers) in the system or fluid to determine an amount of the scale-inhibiting polymer composition in the system or fluid; and (c) periodically or continuously further adding more or removing a portion of the scale-inhibiting polymer composition to or from the system or fluid when the measured amount of tagging units (i.e., first monomers) is less than or greater than, respectively, a predetermined value.

In some embodiments, the methods for determining an amount of a scale-inhibiting polymer composition for inhibiting scale formation include introducing an effective scale-inhibiting amount of a scale-inhibiting polymer composition to an aqueous medium; collecting a sample of the aqueous medium; measuring a fluorescence signal of the sample; and determining an amount of the scale-inhibiting polymer composition based on the fluorescence signal.

In some embodiments, an effective scale-inhibiting amount is an amount sufficient to inhibit calcium carbonate, calcium sulfate, barium sulfate, strontium sulfate, halite, iron sulfide, magnesium carbonate, barium carbonate, strontium carbonate, calcium fluoride, magnesium hydroxide, silica, silicate scales, lead sulfide, vivianite, struvite and/or calcium phosphate scale formation; and/or other carbonate, sulfate, and/or phosphate containing scales.

In some embodiments, when the measured amount of a tagging first monomer (or the scale-inhibiting polymer composition) in a system or fluid being treated is less than a predetermined value, more scale-inhibiting polymer composition may be added to the system or fluid. The predetermined value of scale-inhibiting polymer may be any amount necessary or desired for the particular system or fluid being treated. For example, experiments can be conducted to determine an effective minimum inhibitor concentration (MIC) of scale-inhibiting polymer composition for a particular system or fluid. The phrase "effective minimum inhibitor concentration (MIC)", as used herein, refers to the concentration that just inhibits inorganic scale formation under simulated or actual conditions. The amount of scale-inhibiting polymer composition in a system or fluid may be compared to the MIC value to determine when it may be necessary or desirable to add an additional amount of a scale-inhibiting polymer composition to the system or fluid, or remove a portion of the scale-inhibiting polymer composition from the system or fluid.

In some embodiments, the step of adding the scale-inhibiting polymer composition includes adding a scale-inhibiting polymer composition that includes a scale-inhibiting copolymer as described herein. In some embodiments, adding the scale-inhibiting polymer composition to the system or fluid to be treated includes forcing the scale-inhibiting polymer composition into an oilfield where the fluid is circulating or will be circulated.

A scale-inhibiting polymer composition generally may be added in any amount to produce a necessary or desired effect in a system or fluid to be treated. For example, an effective scale-inhibiting amount of the scale-inhibiting polymer composition may be added to a system or fluid, i.e., an amount capable of reducing or inhibiting the amount of scale in the system by a predetermined amount. In some embodiments, an effective scale-inhibiting amount is an amount sufficient to inhibit calcium carbonate, calcium sulfate, barium sulfate, strontium sulfate, halite, iron sulfide, magnesium carbonate, barium carbonate, strontium carbonate, calcium fluoride, magnesium hydroxide, silica, silicate scales, lead sulfide, and/or calcium phosphate scale formation; and/or other carbonate, sulfate, and/or phosphate containing scales. Generally, scale formation or deposition may occur when scale-forming ions are above the saturation value of a solution and become thermodynamically unstable with respect to precipitation. Ion clusters may begin to form in solution and these clusters eventually attain sufficient density to become physical crystals (also referred to as nucleation). Nucleated crystals may grow and aggregate to form larger crystals. Scale formation or deposition may be controlled by utilizing deposition control agents, or threshold inhibitors, that inhibit precipitation at dosages far below stoichiometric level required for sequestration or chelation. These materials may affect the kinetics of the nucleation and crystal growth of scale-forming salts, and permit supersaturation without scale formation. The effective scale-inhibiting amount of a scale-inhibiting polymer may generally depend on a particular system to be treated and scale-inhibiting moieties in the scale-inhibiting copolymer. For example, the effective scale-inhibiting amount of scale-inhibiting polymer composition in a particular system to be treated may be influenced by factors such as the area subject to deposition, pH, temperature, water quality, the respective concentration in the water of the potential scale and deposit forming species, or a combination thereof.

In some embodiments, a scale-inhibiting polymer composition is effective in a system to be treated when the scale-inhibiting polymer composition is provided at levels less than about 200 parts per million (ppm), less than about 100 ppm, less than about 50 ppm, less than about 35 ppm, less than about 20 ppm, or less than about 10 ppm on the basis of the fluid in a system to be treated. In some embodiments, the scale-inhibitor polymer composition is effective at concentrations of about 0.5 ppm to about 200 ppm, about 0.5 ppm to about 100 ppm, about 0.5 ppm to about 50 ppm, about 0.5 ppm to about 35 ppm, about 0.5 ppm to about 10 parts ppm, about 0.5 ppm to about 3 parts ppm, about 2 ppm to about 10 ppm, or about 4 ppm to about 7 ppm. The scale-inhibiting polymer composition can be added directly into a desired aqueous system to be treated in a fixed quantity or can be added continuously or intermittently to an aqueous system as necessary or desired for the system to be treated. In some embodiments, the level at which the scale-inhibiting polymer composition is provided is the predetermined value of the methods described herein. Other predetermined values may be selected, however.

The polymer compositions herein may be detected (e.g., measured) by any appropriate method, including, but not limited to, fluorometry. In some embodiments, the polymer compositions are detected with a fixed wavelength fluorometer. Detection may be at the polymer maxima excitation (ex) and emission (em) wavelengths. These wavelengths may be determined using a scanning fluorometer in scanning mode. The level of fluorescence may be determined by the Beer-Lambert Law. For example, concentrations may be assigned by comparison of the emission intensity of a polymer composition sample with a calibration plot obtained from polymer samples of a known concentration. Any detection method which utilizes the fluorescence properties of the polymer compositions, particularly the first monomer, may be used, as necessary or desired.

The constituents of a liquid, e.g., water, may be considered when determining the proper application of the scale-inhibiting polymer compositions provided herein, as some of the constituents may have natural fluorescence properties (for example, certain polycyclic hydrocarbons) that may interfere with the detection of the tagging units (i.e., first monomers) of the scale-inhibiting polymer compositions. The chemical properties of produced water may vary considerably depending on the location and the geological formation of an oil field, as well as the type of hydrocarbons being produced. Produced water properties also may vary throughout the lifetime of a reservoir. Most of the naturally fluorescent properties of produced waters typically originate from hydrocarbon residues or other production chemicals in the produced waters. Even though the amount of these species might be minimal, fluorescence can detect these species at very low ppm levels.

In some embodiments, the polymer compositions can be used in combination or alternation with other tagged polymers or tagged polymer compositions, and in particular, with other tagged polymers or tagged polymer compositions including fluorescent moieties that have excitation and/or emission that are different from those of the polymer compositions described herein. The use of the polymer compositions described herein with other tagged polymers or tagged polymer compositions may be referred to as a multi-tagged system. A multi-tagged system could be used, for example, to allow an operator to monitor two different polymers in a system being treated with a polymer composition as provided herein. An example of such a system would include one in which more than one well is drilled and the oil from all wells is collected from one central location. A different polymer composition and/or other tagged polymer may be introduced to each well. From a single sample collected at the central location, an operator may determine which specific well requires more polymer composition and/or other tagged polymer by monitoring the presence and/or concentration of each tagged polymer.

When fluorescent tagging moieties (e.g., first monomers of the polymer compositions provided herein) are present at a sufficiently high concentration, there can be overlap or interference in the fluorescent signals of the different tagging moieties. However, often the squeeze campaigns in oilfields are performed simultaneously to different wells connected to the same wellhead. In some embodiments, the tagged polymers (e.g., first monomers of the polymer compositions) have similar adsorption/desorption profiles. Therefore, if the wells are producing equal amounts of water, the scale-inhibitor levels in each separate well would continue to stay approximately on the same level. In some embodiments, the polymer compositions can be detected in the same water at a level of up to about a 40 ppm to about a 200 ppm difference in scale inhibitor concentrations. In some embodiments, the polymer compositions can be detected in the same water at a level of up to about a 1 ppm to about a 200 ppm, about a 5 ppm to about a 200 ppm, about a 10 ppm to about a 200 ppm, or about a 15 ppm to about a 200 ppm difference in scale inhibitor concentrations. In some embodiments, the polymer compositions can be detected in the same water at a level of up to about a 40 ppm to about a 50 ppm difference in scale inhibitor concentrations. In some embodiments, the difference of concentration could be as low as about a 1 ppm to about a 15 ppm level, about a 5 ppm to about a 15 ppm level, or about a 10 ppm to about a 15 ppm level.

In some embodiments, the polymer compositions are combined in a multi-tagged system with one or more polymers having a different tagging unit than the polymer compositions. Exemplary tagging units are described, for example, in one or more of the following references (each of which is incorporated herein by reference): U.S. Pat. Nos. 7,703,516; 7,943,058; 9,902,904; EP 1 636 142; EP 1 639 228; U.S. Patent Application Publication. No. 2012/0032093.

As used herein, the phrase "effective detection amount" refers to an amount of tagging units (i.e., first monomer) sufficient to provide suitable detection in a particular application. In some embodiments, the polymer composition includes an effective detection amount of tagging units (i.e., first monomer). In some embodiments, an effective detection amount of the first monomer in the polymer compositions is about 0.01% to about 30%, about 0.01% to about 20%, about 0.01% to about 15%, about 0.01% to about 10%; about 0.01% to about 8%; about 0.01% to about 7%; about 0.01% to about 5%; about 0.01% to about 3%, about 0.01% to about 2%, about 0.01% to about 1.5%, about 0.01% to about 1%, about 0.01% to about 0.75%, or about 0.01% to about 0.5%, by weight, based on the total weight of the polymer composition. An effective detection amount may be achieved by the amount of first monomer that is polymerized with an at least one second monomer to form a copolymer, an amount of unpolymerized first monomer added to a polymer composition, or a combination thereof.

The performance or efficacy of polymer compositions may be evaluated using any known methods for anti-scalant or scale inhibitor performance testing, including but not limited to: static anti-precipitation (jar tests), crystal growth kinetics, rotation tests and dynamic scale inhibition tests, for example dynamic tube blocking test, stirred vessel test, and rotating spindle test.

A variety of systems, including aqueous systems, may be treated for scale using the methods described herein. Non-limiting examples of such systems include boiler water, cooling water, seawater (e.g., in oil platform applications), brackish water, oilfield water (e.g., topside and/or downhole), municipal treatment plant water, and industrial treatment plant water. The amount of polymer composition that is effective to treat scale in a particular aqueous system may be determined by routine experimentation in light of the guidance provided herein. The amount of polymer composition added to the aqueous system may vary over a relatively broad range, depending on the nature of the aqueous system and the type of scale. For example, the amount of polymer added to the aqueous system may be in the range of about 0.1 part per million to about 50,000 parts per million, about 0.1 part per million to about 25,000 parts per million, about 0.1 part per million to about 10,000 parts per million, about 0.1 part per million to about 1,000 parts per million, about 0.1 part per million to about 500 parts per million, or about 100 parts per million to about 200 parts per million, based on the capacity of the aqueous system. Various kinds of scale may be treated in accordance with the methods described herein, including without limitation calcium carbonate, calcium sulfate, barium sulfate, strontium sulfate, halite, iron sulfide, magnesium carbonate, barium carbonate, strontium carbonate, calcium fluoride, magnesium hydroxide, silica, silicate scales, lead sulfide, vivianite, struvite and/or calcium phosphate scale formation; and/or other carbonate, sulfate, and/or phosphate containing scales.

For example, the polymer compositions and methods may be used in systems and fluids, such as oilfield injection and production waters, including topside, downhole and rock formation squeeze applications at the well site. In oilfield injection and production waters, scale formation can constrict injection lines, flow lines, and tubing strings. Without wishing to be limited by any particular theory, embodiments of the polymer compositions provided herein can modify the crystal growth of nucleating scale particles, thereby interrupting and delaying crystal growth. Embodiments of the polymer compositions also or alternatively may sequester metal ions, making them unavailable for ion pairing with anions, thereby preventing precipitation of insoluble scale.

In some embodiments, the polymer compositions are utilized in a squeeze application. For example, the polymer compositions may be diluted in a suitable carrier liquid (usually brine), and propagated to an optimized radial distance into the oil producing formation, where it may be retained and then released slowly back into the aqueous phase during normal well production. In some embodiments, the squeeze process includes applying a dilute solution of a scale-inhibiting polymer composition that includes a surfactant (0.1 wt. %) to clean and cool the near wellbore. Once cleaned, a high concentration solution of the scale-inhibiting polymer composition at between about 5% and about 20%, by weight, may be introduced, followed by a lower concentration solution of the scale-inhibiting polymer composition. The solutions are left in contact with the reservoir for a period of time effective to allow for adsorption equilibration, after which the well is returned to production. Adhesion to the formation may allow the scale-inhibiting polymer composition to remain within the near-wellbore area and to resist being pumped in the oil/water emulsion. Although squeeze application of the chemical is a common method of treating downhole scale, the scale-inhibiting polymer compositions herein could be applied by other techniques commonly used offshore, including gas-lift injection, downhole annulus injection, encapsulation or soluble matrix techniques, subsea wellhead injection via umbilical or secondary topside treatments to enhance inhibitor performance as process conditions can vary scaling tendencies.

In some embodiments, a scale-inhibiting polymer composition provided herein is used in a squeeze process wherein after a high concentration solution of the scale-inhibiting polymer composition is applied, an overflush stage is used to place the solution of scale-inhibiting polymer composition to the desired depth of a reservoir. In some embodiments, the reservoir contains a low concentration solution of the scale-inhibiting polymer composition.

In some embodiments, the methods herein include a method for treating scale in a boiler water system. For example, the methods may include adding an exemplary scale-inhibiting polymer composition as described herein to boiler water in need of scale treatment, in an effective scale-inhibiting amount to reduce or inhibit scale in the boiler water, as necessary or desired. In one embodiment, the boiler water scale includes a calcium carbonate, silica, calcium phosphate, or a combination thereof.

In some embodiments, the methods herein include a method for treating scale in a cooling water system. The methods may include adding an exemplary scale-inhibiting polymer composition as described herein to cooling water in need of scale treatment, in an effective scale-inhibiting amount to reduce or inhibit scale in the cooling water, as necessary or desired. For example, the scale-inhibiting polymer composition may be added to the water used in a cooling tower. In some embodiments, the cooling water scale includes a calcium carbonate.

In some embodiments, the methods herein include a method for treating scale in a brackish water, reuse water, or seawater system. The methods may include adding an exemplary scale-inhibiting polymer composition as described herein to at least one of brackish water and seawater in need of scale treatment, in an effective scale-inhibiting amount to reduce or inhibit scale in the brackish water and/or seawater, as necessary or desired. For example, the scale-inhibiting polymer composition may be added to the process water of a desalination plant, such as a thermal or membrane desalination plant. In some embodiments, the brackish water and/or seawater scale include a calcium sulfate, calcium phosphate, silica, magnesium hydroxide, calcium carbonate, or a combination thereof.

In some embodiments, the methods herein include a method for treating scale in an oilfield water system. The methods may include adding an exemplary scale-inhibiting polymer composition as described herein to oilfield water in need of scale treatment, in an effective scale-inhibiting amount to reduce or inhibit scale in the oilfield water, as necessary or desired. For example, the scale-inhibiting polymer composition may be added to process water on an oil platform. The oilfield water may be downhole water that is pumped underground (e.g., for enhanced oil recovery) and/or may be used to treat topside oilfield water. In some embodiments, the oilfield water scale includes a sulfate salt, e.g., barium sulfate, strontium sulfate, or a combination thereof.

In some embodiments, the methods provided herein include a method for treating scale in a municipal water treatment system. The methods may include adding an exemplary scale-inhibiting polymer composition as described herein to municipal treatment plant water in need of scale treatment, in an effective scale-inhibiting amount to reduce or inhibit scale in the municipal treatment plant water, as necessary or desired. For example, the scale-inhibiting polymer composition may be added to the process water of a plant that treats water to render it suitable for municipal drinking water, and/or to a plant that treats municipal waste water. In some embodiments, the municipal treatment plant water scale includes a calcium carbonate and/or phosphate, e.g., at least one of struvite and vivianite.

Generally, the scale-inhibiting polymer compositions and/or methods provided herein may be used in for scale treatment in oil or gas applications, for example water injection, production zones, top-side operations, pipelines, and tankage; in pulp or paper applications, for example digestors, headbox, showers and bleach plants; in municipal or industrial applications, for example desalination, cooling towers, sugar refining, and waste treatment; and in metals or mining applications, for example heap leaching, carbon circuits, slurry transport, and digestors. In some embodiments, the scale-inhibiting polymer compositions are for use in a reverse osmosis system.

In some embodiments, the scale-inhibiting polymer compositions and/or methods are used to treat scale associated with biofilms or microbiologically-influenced corrosion, for example, manganese related corrosion of stainless steel by manganese depositing biofilms. The term "biofilm", as used herein, refers to an aggregate of microorganisms in which cells adhere to each other and/or to a surface. The adherent cells can be embedded within a self-produced matrix of extracellular polymeric substance (EPS).

The scale-inhibiting polymers compositions and/or methods described herein may be used to treat scale in any of the foregoing applications.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When methods, compounds, polymers, or compositions are claimed or described in terms of "comprising" various components or steps, the methods, compounds, polymers, or compositions can also "consist essentially of" or "consist of" the various components or steps, unless stated otherwise.

The terms "a," "an," and "the" are intended to include plural alternatives, e.g., at least one. For instance, the disclosure of "a first monomer," "a liquid," "a copolymer", and the like, is meant to encompass one, or mixtures or combinations of more than one first monomer, liquid, copolymer, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, the compounds exhibit fluorescence emission maxima at about 440 nm to about 450 nm. This range should be interpreted as encompassing emission maxima of about 440 nm and about 450 nm, and further encompasses "about" each of 441 nm, 442 nm, 443 nm, 444 nm, 445 nm, 446 nm, 447 nm, 448 nm, and 449 nm, including any ranges and sub-ranges between any of these values.

As used herein, the term "about" means plus or minus 10% of the numerical value of the number with which it is being used.

The present disclosure is further illustrated by the following non-limiting embodiments. In view of these non-limiting embodiments, other aspects will be apparent to those skilled in the art from consideration of the specification and practice of the subject matter disclosed herein.

Embodiment 1. A compound or isomer of Formula (I):

Formula (I)

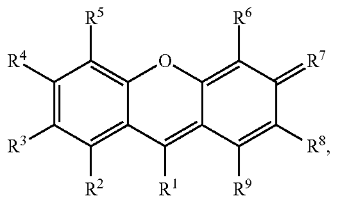

wherein $R^1$ is selected from the group consisting of hydrogen, hydroxyl, and a hydrocarbyl (e.g., a $C_1$-$C_{10}$ hydrocarbyl) optionally substituted with one of more functional groups (e.g., a carboxylic acid moiety or a sulfonic acid moiety), with the proviso that the hydrocarbyl does not include any double bonds that (i) are non-conjugated and (ii) form a direct covalent bond between two carbon atoms; wherein $R^4$ is selected from the group consisting of hydroxyl and —NR'R"; wherein $R^7$ is selected from the group consisting of oxygen, —NR'R", and —NR'; wherein $R^2$, $R^3$, $R^5$, $R^6$, $R^8$, and $R^9$ are independently selected from the group consisting of hydrogen, hydroxyl, alkoxy (e.g., a $C_1$-$C_6$ alkoxy), —N(R')(R"), alkyl (e.g., a $C_1$-$C_6$ alkyl), aryl (e.g., a $C_4$-$C_{14}$ aryl), and halogen; and wherein R' and R" are independently selected from the group consisting of hydrogen and alkyl (e.g., a $C_1$-$C_6$ alkyl).

Embodiment 2. The compound of Embodiment 1, wherein $R^4$ is hydroxyl, $R^7$ is oxygen, and the compound has a structure according to Formula (IA):

Formula (IA)

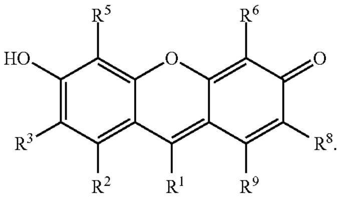

Embodiment 3. The compound of Embodiment 2, wherein $R^2$, $R^3$, $R^5$, $R^6$, $R^8$, and $R^9$ are hydrogen, and the compound has a structure according to Formula (IB):

Formula (IB)

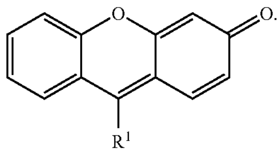

Embodiment 4. The compound of Embodiment 1, wherein $R^4$ is a first —NR'R", $R^7$ is a second —NR'R", wherein the first and second —NR'R" are the same or different, and the compound has a structure according to Formula (IC):

Formula (IC)

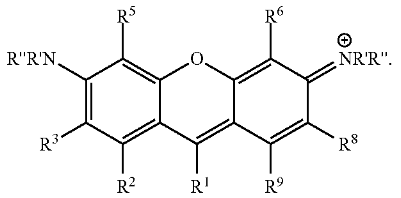

Embodiment 5. The compound of Embodiment 4, wherein the compound is a compound of Formula (IC), wherein $R^2$, $R^3$, $R^5$, $R^6$, $R^8$, and $R^9$ are hydrogen, and the compound has a structure according to Formula (ID):

Formula (ID)

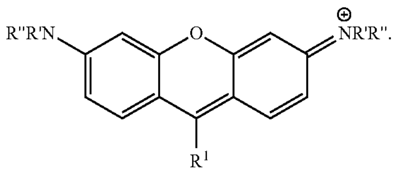

Embodiment 6. The compound of Embodiment 4, wherein each R' and each R" are hydrogen, and the compound has a structure according to Formula (IE):

Formula (IE)

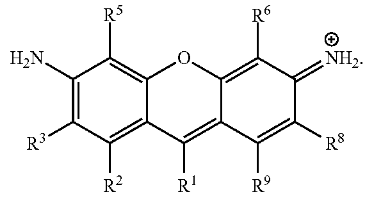

Embodiment 7. The compound of Embodiment 6, wherein $R^2$, $R^3$, $R^5$, $R^6$, $R^8$, and $R^9$ are hydrogen, and the compound has a structure according to Formula (IF):

Formula (IF)

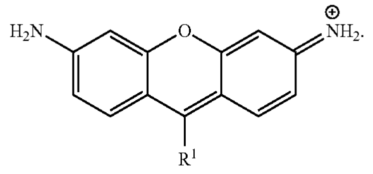

Embodiment 8. The compound of Embodiment 4, wherein each R' and each R" are ethyl, and the compound has a structure according to Formula (IG):

Formula (IG)

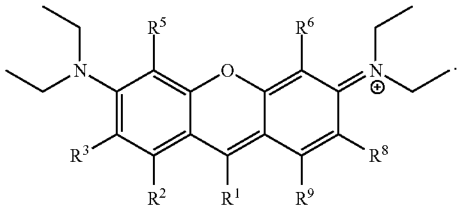

Embodiment 9. The compound of Embodiment 8, wherein $R^2$, $R^3$, $R^5$, $R^6$, $R^8$, and $R^9$ are hydrogen, and the compound has a structure according to Formula (IH):

Formula (IH)

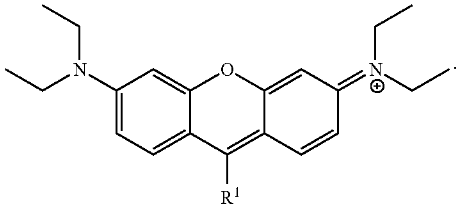

Embodiment 10. The compound of any one of Embodiments 1 to 9, wherein $R^1$ is selected from one of the following moieties, which may be unsubstituted or substituted as described herein—

| $R^1$ | |
|---|---|
| $C_1$-$C_{10}$ hydrocarbyl | $C_1$-$C_{10}$ hydrocarbyl substituted with a carboxylic acid moiety and/or a sulfonic acid moiety |
| $C_1$-$C_9$ hydrocarbyl | $C_1$-$C_9$ hydrocarbyl substituted with a carboxylic acid moiety and/or a sulfonic acid moiety |
| $C_1$-$C_8$ hydrocarbyl | $C_1$-$C_8$ hydrocarbyl substituted with a carboxylic acid moiety and/or a sulfonic acid moiety |
| $C_1$-$C_7$ hydrocarbyl | $C_1$-$C_7$ hydrocarbyl substituted with a carboxylic acid moiety and/or a sulfonic acid moiety |
| $C_1$-$C_6$ hydrocarbyl | $C_1$-$C_6$ hydrocarbyl substituted with a carboxylic acid moiety and/or a sulfonic acid moiety |
| $C_1$-$C_5$ hydrocarbyl | $C_1$-$C_5$ hydrocarbyl substituted with a carboxylic acid moiety and/or a sulfonic acid moiety |
| $C_1$-$C_4$ hydrocarbyl | $C_1$-$C_4$ hydrocarbyl substituted with a carboxylic acid moiety and/or a sulfonic acid moiety |
| $C_1$-$C_3$ hydrocarbyl | $C_1$-$C_3$ hydrocarbyl substituted with a carboxylic acid moiety and/or a sulfonic acid moiety |
| $C_2$-$C_3$ hydrocarbyl | $C_2$-$C_3$ hydrocarbyl substituted with a carboxylic acid moiety and/or a sulfonic acid moiety |
| $-(CH_2)_nCH_3$, wherein n is 1-5 | $-(CH_2)_nCOOH$, wherein n is 1-5 |
| $-(CH_2)_2CH_3$ | $-(CH_2)_2COOH$ |
| $-C_6H_5$ | 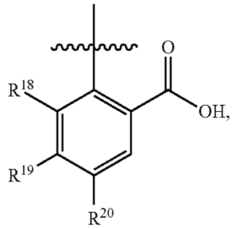 wherein $R^{18}$, $R^{19}$, and $R^{20}$ are independently selected from the group consisting of hydrogen, hydroxyl, $C_1$-$C_6$ alkoxy, $-N(R')(R'')$, $C_1$-$C_6$ alkyl, and $C_4$-$C_{14}$ aryl |
| 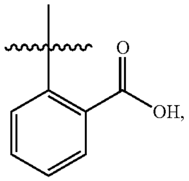 [SMILES: *c1ccccc1C(=O)O] which is referred to herein as "-ortho-$(C_6H_4)COOH$" | |

Embodiment 11. The compound of Embodiment 1, wherein $R^2$, $R^3$, $R^5$, $R^6$, $R^8$ and $R^9$ are hydrogen, $R^4$ is hydroxyl, $R^7$ is oxygen, $R^1$ is $-(CH_2)_2COOH$, and the first monomer is 3-(6-hydroxy-3-oxo-3H-xanthen-9-yl)propanoic acid, a salt, a hydrate, a salt hydrate, a stereoisomer, a dehydrate, a tautomer, or a derivative thereof—

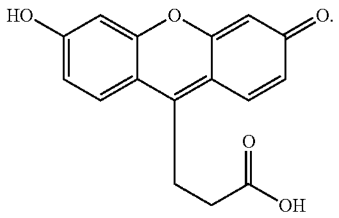 [SMILES: O=C(O)CCc1c2ccc(=O)cc-2oc2cc(O)ccc12]

Embodiment 12. The compound of Embodiment 11, wherein, a tautomer of the 3-(6-hydroxy-3-oxo-3H-xanthen-9-yl)propanoic acid includes 3',6'-dihydroxy-3,4-dihydro-5H-spiro[furan-2,9'-xanthen]-5-one, as depicted in the following scheme:

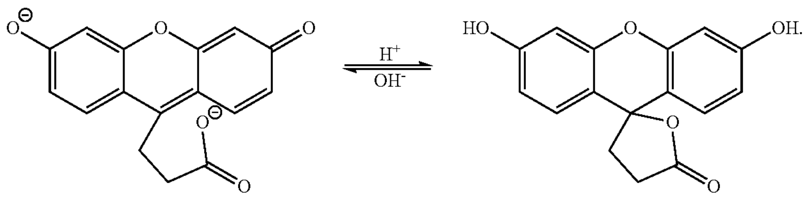

Embodiment 13. The compound of Embodiment 1, wherein $R^2$, $R^3$, $R^5$, $R^6$, $R^8$, and $R^9$ are hydrogen, $R^4$ is hydroxyl, $R^7$ is oxygen, $R^1$ is -ortho-$(C_6H_4)COOH$, and the first monomer is 2-(6-hydroxy-3-oxo-3H-xanthen-9-yl)benzoic acid, a salt, a hydrate, a salt hydrate, a stereoisomer, a dehydrate, a tautomer, or a derivative thereof—

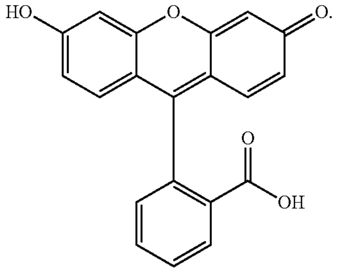 [SMILES: O=C(O)c1ccccc1-c1c2ccc(=O)cc-2oc2cc(O)ccc12]

Embodiment 14. The compound of Embodiment 1, wherein $R^1$ is -ortho-$(C_6H_4)COOH$, $R^2$, $R^3$, $R^5$, $R^6$, $R^8$, and $R^9$ are hydrogen, $R^4$ and $R^7$ are —NR'R", wherein R' and R" are ethyl, and the first monomer is N-(9-(2-carboxyphenyl)-6-(diethylamino)-3H-xanthen-3-ylidene)-N-ethylethanaminium, a hydrate, a salt hydrate, a stereoisomer, a dehydrate, a tautomer, or a derivative thereof—

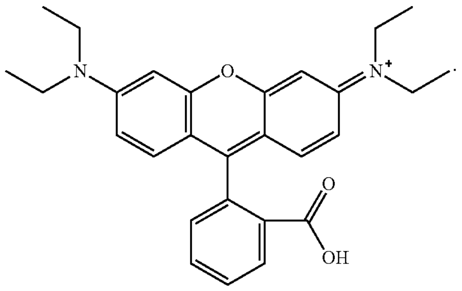 [SMILES: CCN(CC)c1ccc2c(-c3ccccc3C(=O)O)c3ccc(=[N+](CC)CC)cc-3oc2c1]

Embodiment 15. The compound of any one of Embodiments 1 to 14, wherein (i) a positively charged atom or moiety of the compound of any one of Embodiments 1 to 14 is associated with an anion comprising an inorganic anion, such as a halide (e.g., $Cl^-$), (ii) none of $R^1$, $R^2$, $R^3$, $R^4$, $R^5$, $R^6$, $R^7$, $R^8$, and $R^9$ includes any double bonds, (iii) none of $R^1$, $R^2$, $R^3$, $R^4$, $R^5$, $R^6$, $R^7$, $R^8$, and $R^9$ includes any double bonds that (a) are non-conjugated and (b) form a direct covalent bond between two carbon atoms, (iv) none of $R^1$, $R^2$, $R^3$, $R^5$, $R^6$, $R^8$, and $R^9$ includes any double bonds, (v) none of $R^1$, $R^2$, $R^3$, $R^5$, $R^6$, $R^8$, and $R^9$ includes any double bonds that (a) are non-conjugated and (b) form a direct covalent bond between two carbon atoms, (vi) $R^1$ does not include any double bonds, or (vii) a combination thereof.

Embodiment 16. A polymer composition comprising a copolymer, wherein the copolymer comprises a first monomer selected from a compound of any one of Embodiments 1 to 15, wherein the first monomer is a tagging monomer.

Embodiment 17. The polymer composition of Embodiment 16, further comprising at least one second monomer comprising at least one polymerizable double bond or at least one polymerizable triple bond, wherein the at least one second monomer is a scale-inhibiting monomer.

Embodiment 18. The polymer composition of Embodiment 17, wherein the at least one second monomer comprises (a)(i) sodium allyl sulfonate and (ii) at least one of maleic acid, maleic anhydride, or acrylic acid; or (b) at least one of maleic acid, maleic anhydride, or acrylic acid.

Embodiment 19. The polymer composition of Embodiment 17 or 18, wherein the at least one second monomer comprises a compound of Formula (II):

Formula (II)

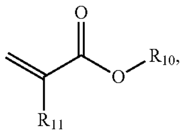

wherein $R^{10}$ and $R^{11}$ are independently selected from the group consisting of hydrogen and alkyl (e.g., a $C_1$-$C_6$ alkyl).

Embodiment 20. The polymer composition of Embodiment 19, wherein $R^{10}$ and $R^{11}$ are hydrogen.

Embodiment 21. The polymer composition of Embodiment 19, wherein $R^{11}$ is an unsubstituted $C_1$ alkyl, and $R^{10}$ is hydrogen.

Embodiment 22. The polymer composition of any one of Embodiments 16 to 21, wherein the at least one second monomer includes an allylsulfonate salt; acrylic acid; vinyl sulfonic acid; a vinyl sulfonate salt; vinyl phosphoric acid; a vinyl phosphonate salt; vinylidene diphosphonic acid or a salt thereof; methacrylic acid; vinyl acetate; vinyl alcohol; vinyl chloride; an unsaturated mono- or di-carboxylic acid or anhydride; vinyl chloride; styrene-p-sulfonic acid, or a styrene sulfonates salt; acrylamido-2-methylpropanesulfonic acid (AMPS); hydroxyphosphonoacetic acid (HPA); a hypophosphorus acid; an acrylamide; propargyl alcohol; butyr-1,4-diol; or a combination thereof.

Embodiment 23. The polymer composition of any one of Embodiments 16 to 22, wherein the first monomer is present in the copolymer at an amount of about 0.01% to about 30%, about 0.01% to about 20%, about 0.01% to about 15%, about 0.01% to about 10%; about 0.01% to about 8%; about 0.01% to about 7%; about 0.01% to about 5%; about 0.01% to about 3%, or about 0.01% to about 2%, by weight, 0.01% to about 1.5%, about 0.01% to about 1%, about 0.01% to about 0.75%, or about 0.01% to about 0.5%, by weight, based on the weight of the copolymer.

Embodiment 24. The polymer composition of any one of Embodiments 16 to 23, wherein the copolymer of the polymer composition has a weight average molecular weight of about 500 Daltons to about 20,000 Daltons, about 1200 Daltons to about 15000 Daltons, about 2000 Daltons to about 10000 Daltons, about 2000 Daltons to about 8000 Daltons, about 2000 Daltons to about 6000 Daltons, about 2000 Daltons to about 4000 Daltons, or about 2000 Daltons to about 3000 Daltons.

Embodiment 25. The polymer composition of any one of Embodiments 16 to 24, further comprising one or more other groups resulting from a polymerization initiator, end-capping groups, or a combination thereof.

Embodiment 26. A method for forming a condensation product, wherein the condensation product includes a compound of any one of Embodiments 1 to 15, and the methods includes contacting an aryl alcohol, a condensation catalyst, and a compound according to Formula (A) or Formula (B) to form the condensation product;

Formula (A)

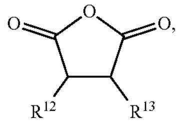

Formula (B)

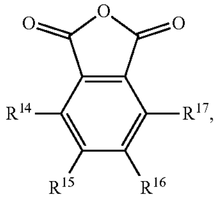

wherein $R^{12}$, $R^{13}$, $R^{14}$, $R^{15}$, $R^{16}$, and $R^{17}$ are independently selected from the group consisting of hydrogen, hydroxyl, and alkyl (e.g., a $C_1$-$C_6$ alkyl).

Embodiment 27. The method of Embodiment 26, wherein $R^{12}$ and $R^{13}$ are hydrogen, and the compound of Formula (A) is dihydrofuran-2,5-dione, i.e., succinic anhydride:

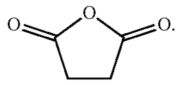

Embodiment 28. The method of Embodiment 26, wherein $R^{14}$, $R^{15}$, $R^{16}$, and $R^{17}$ are hydrogen, and the compound of Formula (B) is isobenzofuran-1,3-dione:

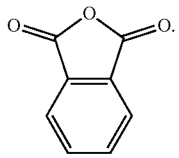 [SMILES: O=C1OC(=O)c2ccccc21]

Embodiment 29. The method of any one of Embodiments 26 to 28, wherein the aryl alcohol includes (i) an aryl moiety, and (ii) at least one hydroxyl moiety.

Embodiment 30. The method of Embodiment 29, wherein the aryl alcohol includes two hydroxyl moieties.

Embodiment 31. The method of Embodiment 30, wherein the aryl alcohol is resorcinol, 1,6-dihydroxynaphthalene, or a combination thereof.

Embodiment 32. The method of any one of Embodiments 26 to 31, wherein the condensation catalyst is a Lewis acid.

Embodiment 33. The method of Embodiment 32, wherein the Lewis acid is selected from the group consisting of $ZnCl_2$, $FeCl_3$, $AlCl_3$, and $BCl_3$.

Embodiment 34. The method of any one of Embodiments 26 to 33, wherein the condensation catalyst is a sulfonic acid.

Embodiment 35. The method of Embodiment 34, wherein the sulfonic acid is a $C_1$-$C_6$ alkyl sulfonic acid, a $C_5$-$C_{14}$ aryl sulfonic acid, or a combination thereof.

Embodiment 36. The method of Embodiment 35, wherein the $C_1$-$C_6$ alkyl sulfonic acid is methanesulfonic acid ($MeSO_3H$), p-toluenesulfonic acid, or a combination thereof.

Embodiment 37. The method of any one of Embodiments 26 to 36, wherein the contacting of the aryl alcohol, the condensation catalyst, and the compound of Formula (A) or Formula (B) occurs at a temperature of about 25° C. to about 200° C., about 50° C. to about 150° C., about 75° C. to about 150° C., about 100° C. to about 150° C., or about 100° C. to about 125° C.

Embodiment 38. The method of any one of Embodiments 26 to 37, wherein the contacting of the aryl alcohol, the condensation catalyst, and the compound of Formula (A) or Formula (B) occurs at ambient pressure.

Embodiment 39. The method of any one of Embodiments 26 to 38, further comprising contacting the condensation product with at least one second monomer to form the copolymer of any one of Embodiments 16 to 25.

Embodiment 40. A method of forming a copolymer of any one of Embodiments 16 to 25, comprising providing a compound of any one of Embodiments 1 to 15, and contacting the compound of any one of Embodiments 1 to 15 with at least one second monomer of any one of Embodiments 17 to 22.

Embodiment 41. The method of Embodiment 39 or 40, wherein the method comprises a radical polymerization.

Embodiment 42. The method of any one of Embodiments 39 to 41, wherein the contacting of the compound of one of Embodiments 1 to 15 with the at least one second monomer occurs in the presence of one or more polymerization initiators.

Embodiment 43. The method of Embodiment 42, wherein the one or more polymerization initiators comprises one or more inorganic peroxides; organic peroxides; azo compounds; tetrakis(hydroxymethyl)phosphonium sulfate (THPS); cerium ammonium nitrate; perchlorates; triphenylphosphine; or a combination thereof.

Embodiment 44. The method of Embodiment 42, wherein the one or more polymerization initiators is selected from the group consisting of ammonium persulfate, tert-butyl hydroperoxide, and 4,4'-azobis(4-cyanovaleric acid).

Embodiment 45. A method for preventing or reducing scale formation, the method comprising providing a system comprising a fluid in circulation, wherein the fluid comprises a scale-inhibiting polymer composition of any one of Embodiments 16 to 25; measuring with an analytical technique an amount of the first monomer in the system or the fluid to determine an amount of the polymer composition in the system or the fluid, wherein the measuring is performed periodically or continuously.

Embodiment 46. The method of Embodiment 45, wherein the method further comprises (i) adding an additional amount of the polymer composition to the system or the fluid if the amount of the polymer composition in the system or the fluid is less than a predetermined value, or (ii) removing a portion of the polymer composition from the system or the fluid if the amount of the polymer composition in the system or the fluid is greater than the predetermined value.

Embodiment 47. The method of Embodiment 45 or 46, wherein the scale-inhibiting polymer composition in the system is provided at levels less than about 200 parts per million (ppm), less than about 100 ppm, less than about 50 ppm, less than about 35 ppm, less than about 20 ppm, or less than about 10 ppm on the basis of the fluid in the system.

Embodiment 48. The method of Embodiment 45 or 46, wherein the scale-inhibitor polymer composition in the system is provided at an amount of about 0.5 ppm to about 200 ppm, about 0.5 ppm to about 100 ppm, about 0.5 ppm to about 50 ppm, about 0.5 ppm to about 35 ppm, about 0.5 ppm to about 10 parts ppm, about 0.5 ppm to about 3 parts ppm, about 2 ppm to about 10 ppm, or about 4 ppm to about 7 ppm.

Embodiment 49. The method of any one of Embodiments 45 to 48, wherein the system is an aqueous system.

Embodiment 50. The method of Embodiment 49, wherein the system includes boiler water, cooling water, seawater, brackish water, oilfield water, desalination water (e.g., thermal and/or membrane desalination), food, beverages, municipal treatment plant water, or industrial treatment plant water.

Embodiment 51. The (i) method of any one of Embodiments 26 to 38, (ii) the method of any one of Embodiments 39 to 44, (iii) the polymer composition of any one of Embodiments 16 to 25, and/or (iv) the compound of any one of Embodiments 1 to 15, wherein any one or more compounds of Embodiments 1 to 15 is excluded.

Embodiment 51. The polymer composition or method of any one of the preceding embodiments, wherein the first monomer is present at least as an end group.

Embodiment 52. The polymer composition or method of Embodiment 51, wherein the first monomer is bonded to a polymer via a carbon atom at the 2', 4', 5', or 7' position of the compound of formula (I).

EXAMPLES

The present disclosure is further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects will be apparent to those skilled in the art from consideration of the specification and practice of the subject matter disclosed herein.

Example 1—Synthesis of "Resorcinsuccinic Anhydride Derivative"

The following examples describe embodiments of fluorescent tags that were attached to a polymer by a radical reaction in polymerization.

The attachment of the tags, as explained in the following examples, was verified by size exclusion chromatography (UV detection) and fluorescence measurements. The tags permitted quantification of the polymer concentration by a sensitive and specific fluorescence measurement.

Resorcinsuccinic (i.e., 3',6'-dihydroxy-3,4-dihydro-5H-spiro[furan-2,9'-xanthen]-5-one) was synthesized via a condensation reaction of succinic anhydride (i.e., dihydrofuran-2,5-dione oxolane-2,5-dione) and resorcinol using para-toluenesulfonic acid (p-TosOH*$H_2O$) as a catalyst under $N_2$.

11.31 grams of resorcinol, 5.16 grams of succinic anhydride, and 1,961 grams of p-TosOH*$H_2O$ were weighed in a 4-neck 250 mL round-bottom flask equipped with a reflux condenser. The mixture was stirred with a magnetic stirrer, and heated to reaction temperature. The reaction proceeded first at 100° C. for 15 minutes, then at 120° C. for 1 hour, and finally at 140° C. for 1.5 hours.

The product was then cooled to room temperature, and crystallized from methanol. The reaction was considered to proceed according to the following scheme:

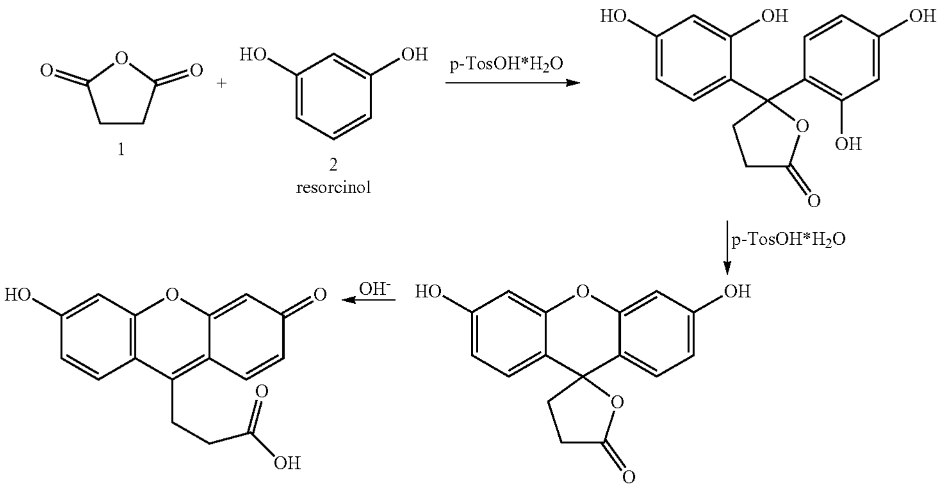

1

2
resorcinol

The product prepared by this example was a fluorescent molecule (having an excitation max of ~490 nm, an emission max of about 500-505 nm, and was fluorescent active in alkali).

Example 2—Process for Tagging a Polymer

The resorcinsuccinic tagged scale inhibiting polymers of this example were prepared by the following steps.

First, a reactor was charged with the given amounts of resorcinsuccinic of Example 1, sodium allyl sulfonate (SAS), maleic anhydride terpolymer (MA), and ethylenediaminetetraacetic acid (EDTA). The amounts depended on the weight percent of resorcinsuccinic tagging moiety desired. For example, about 225 g of 25 w-% aqueous SAS, about 42 g MA, about 3.6 g of 40 w-% aqueous EDTA, and about 0.1 g resorcinsuccinic were used in one test.

The reactor was protected from light and the reaction was conducted in a nitrogen atmosphere. The contents of the reactor were stirred and heated to about 104° C. An initiator solution (containing about 7.2 g ammonium persulfate in about 20.9 g water) was fed into the reactor over several hours. Once the addition was complete, the system was kept at about 104° C. for 30 minutes. The resulting polymer solution was cooled to room temperature.

Not wishing to be bound by any particular theory, it is believed that the resorcinsuccinic "first monomer" of Example 1 attached to the polymer of this example at least as an end group. Although any atom of the resorcinsuccinic may be reactive, it is believed that carbon atoms 2', 4', 5', and 7' of the resorcinsuccinic are most likely to react with a macroradical. Therefore, a polymer of this example may have the following generic structure, but other structures may be possible:

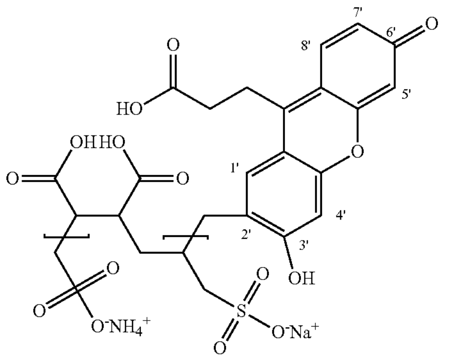

Tagged polymers prepared by this example were fluorescent molecules (having an excitation max ~490-500 nm, an emission max ~510-520 nm, and were fluorescent active in alkali). Slight shifts (about 8 nm) in excitation and emission maxima were observed when the tag was attached to the polymer.

Example 3—Evaluation of Tag's Yield to Polymer

The attachment of the tag of Example 1 to the polymer backbone, as described at Example 2, was estimated by comparing the fluorescence yield of clean and uncleaned samples.

The samples were cleaned with a NAP™-25 size-exclusion chromatography (SEC) column (GE Healthcare, USA). The SEC column permitted polymeric materials to be separated from unattached tag monomers.

As depicted at FIG. 1, about 95% (by weight) of the resorcinsuccinic tag was incorporated into the polymer backbone. FIG. 1 depicts fluorescence emission maxima of resorcinsuccinic (condensation product of resorcinol and succinic anhydride) tagged polymer (in mQ, basified to pH 14). FIG. 1 depicts data for an unpurified sample, and a sample purified with the NAP size exclusion column.

Figure 2:
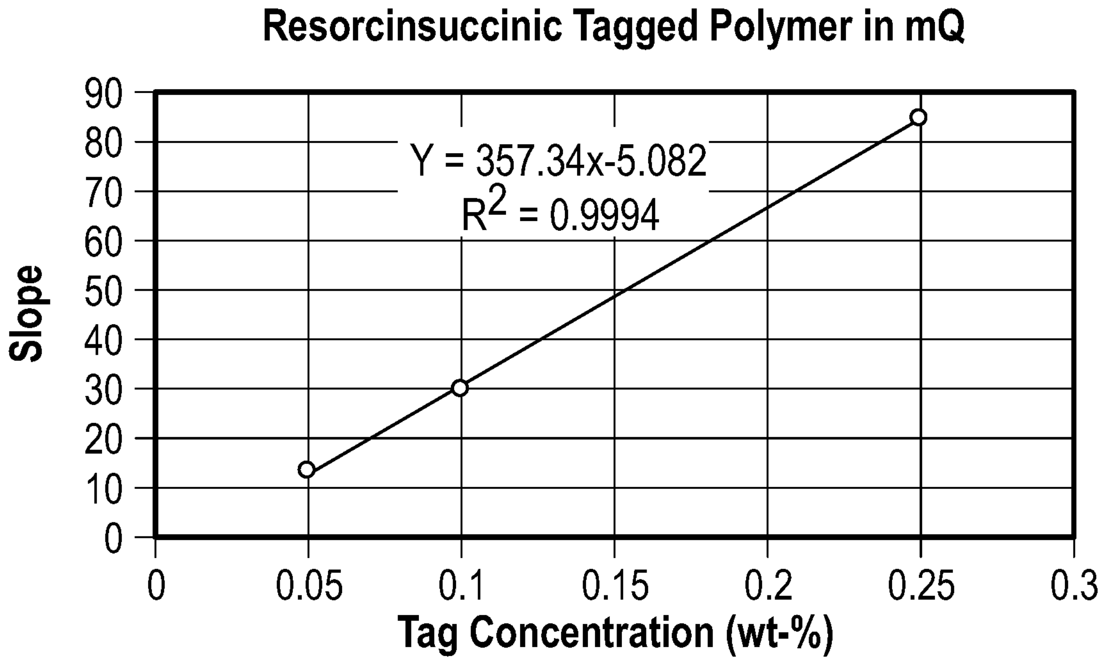
FIG. 2 depicts a calibration curve for one embodiment of a polymer tagged with an embodiment of a tagging agent described herein.

FIG. 2 depicts the calibration curve slope of the resorcinsuccinic tagged polymer of Example 2 as a function of tag concentration (0.05-0.25 wt-%). The slope of the calibration curve (in the dynamic range) increased linearly with increasing tag concentration. Therefore, the detection limit and dynamic measurement range of the tagged polymer could be adjusted by adjusting the tag concentration.

Example 4—Further Measurement Results

Figure 3:
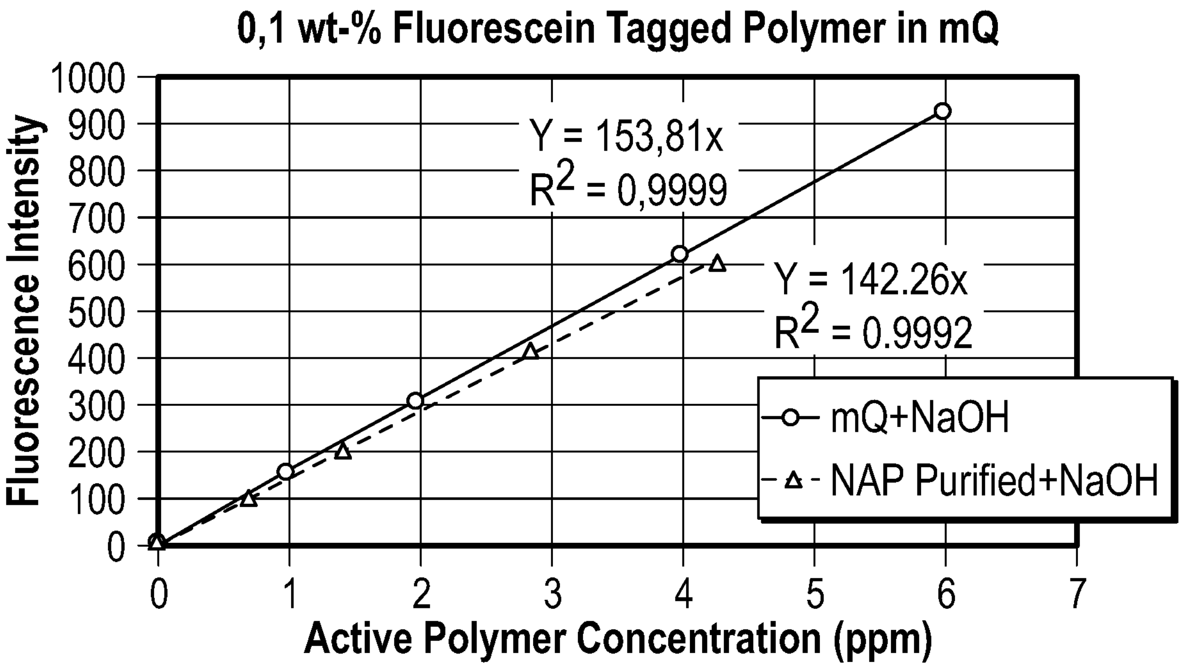
FIG. 3 depicts fluorescence emission maxima of one embodiment of a polymer tagged with an embodiment of a tagging agent described herein.

FIG. 1 and FIG. 3 present the fluorescence emission maxima of resorcinsuccinic (see Scheme 1) and fluorescein (see Scheme 2) tagged polymer, respectively. Specifically, FIG. 3 depicts fluorescence emission maxima of an embodiment of a fluorescein tagged polymer (in mQ, basified to pH 14). Data from an unpurified sample and a sample purified with NAP size exclusion column are depicted.

Scheme 1 - Resorcinsuccinc

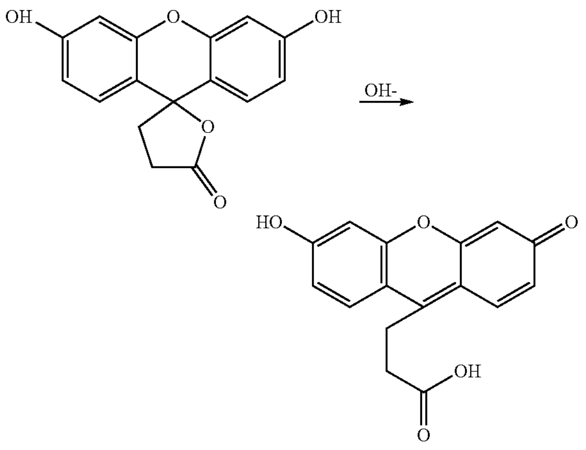

Em(max) 504 nm

Scheme 2 - Fluorescein

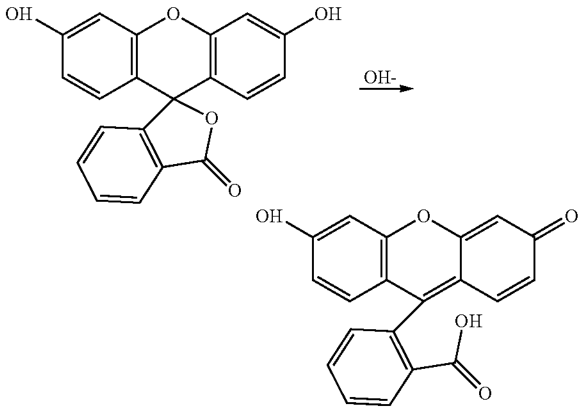

The dyes were attached to a polymer via radical reaction in the polymerization. The dye concentrations of the samples of this example were 0.1 wt-%, but, as described herein, other concentrations are envisioned.

The tagged polymers were diluted in mQ and basified with NaOH (pH 14) for the measurement. The circles represent the emission maxima of products without purification, whereas the triangles represent the emission maxima of products which were purified with illustra NAP™ gravimetric flow columns (GE Healthcare, USA).

The operation mechanism of NAP gravimetric columns is based on size exclusion: larger molecules eluted first whereas smaller impurities were retained in the column. Therefore, it was expected that an attached dye should migrate through the column together with the polymer, whereas an unattached tag should be retained in the column.

The fluorescence emission maxima of NAP purified samples were almost the same as that of the unpurified sample, verifying that most of the fluorescein and resorcinsuccinic dyes were attached to the polymer.

The curves (emission intensity maxima vs. active polymer concentration) were linear in the studied concentration range and the slopes were relatively high. The high sensitivity permitted detection of tagged polymers in low concentration.

Figure 4:
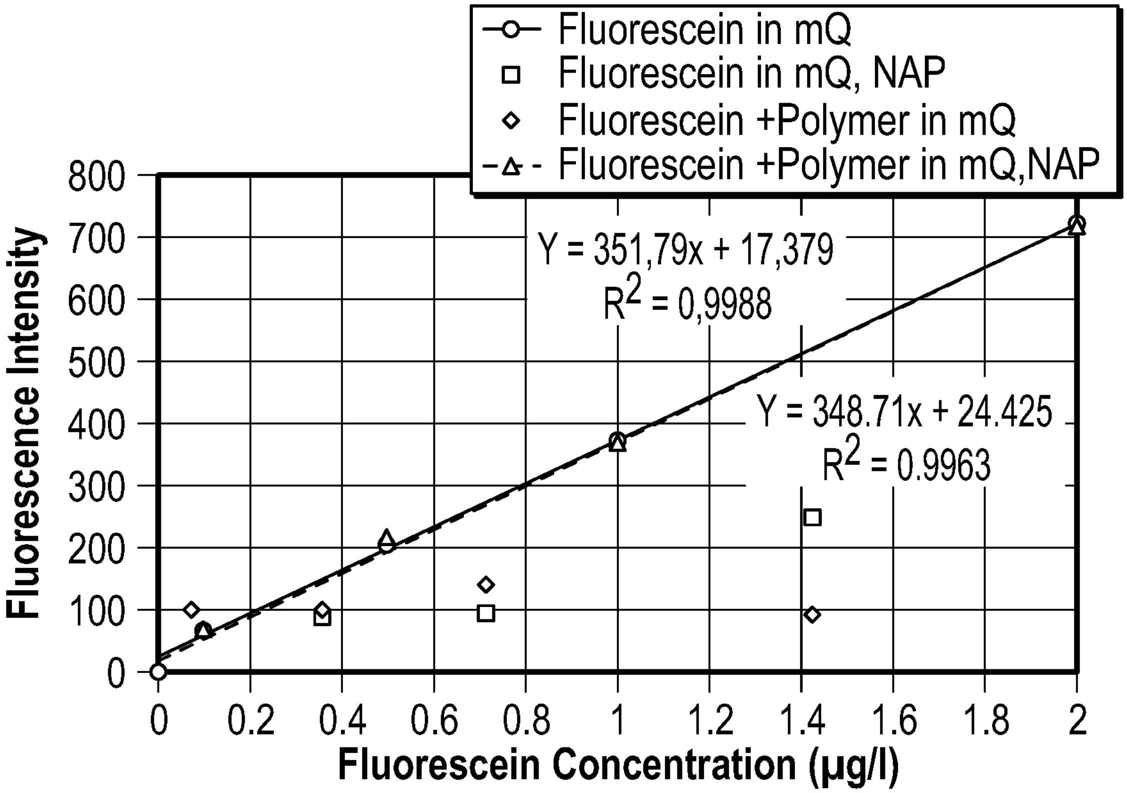
FIG. 4 depicts the fluorescence emission maxima of fluorescein and fluorescein mixed with an embodiment of a polymer.

FIG. 4 depicts the fluorescence emission maxima of fluorescein and fluorescein mixed with the polymer. Specifically, FIG. 4 depicts fluorescence emission maxima of fluorescein (circles) and fluorescein mixed with the polymer (triangles). The emission maxima of unpurified and NAP size exclusion column purified samples are depicted by the shaded (e.g., ▲) and unshaded (e.g., Δ) symbols, respectively.

Fluorescein dye was dissolved in mQ $H_2O$ and basified with NaOH (pH 14) for the measurement (shaded circles). In another sample, fluorescence emission maxima of fluorescein dye mixed with an un-tagged polymer (KEMGUARD™ 2253 (Kemira Oyj, Finland)) was measured (shaded triangles). The tagged polymer did not affect the fluorescence emission intensity of the fluorescein. The tagged polymer also did not change the excitation and emission maxima (490 nm and 512 nm, respectively) of fluorescein.

The unshaded circles depict the fluorescence emission maxima of samples, which were purified with illustra NAP™ gravimetric flow columns (GE Healthcare, USA). Unattached fluorescein was expected to be retained in the size exclusion column, whereas the polymer was expected to migrate through the column. It was observed that the fluorescence emission maxima of samples which had been purified with NAP column were low, verifying that fluorescein was not attached to the polymer by merely mixing the dye and polymer together.

We claim:

1. A polymer composition comprising:

a copolymer comprising—

(i) a first monomer selected from the group consisting of a compound or isomer of Formula (I), a salt, a hydrate, a salt hydrate, a stereoisomer, a dehydrate, a tautomer, or a derivative thereof, wherein the first monomer is a tagging monomer, and (ii) at least one second monomer comprising at least one polymerizable double bond or at least one polymerizable triple bond, wherein the at least one second monomer is a scale-inhibiting monomer;

Fomula (I)

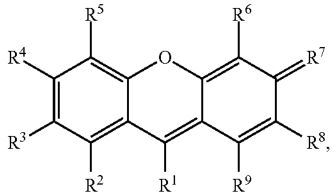

wherein $R^1$ is —$(CH_2)_2COOH$;

wherein $R^4$ is hydroxyl and $R^7$ is oxygen;

wherein $R^2$, $R^3$, $R^5$, $R^6$, $R^8$, and $R^9$ are independently selected from the group consisting of hydrogen, hydroxyl, alkoxy, —N(R')(R"), alkyl, aryl, and halogen; and wherein R' and R" are independently selected from the group consisting of hydrogen and alkyl.

2. The polymer composition of claim 1, wherein the first monomer is present in the copolymer at an amount of about 0.01% to about 5%, by weight, based on the weight of the copolymer, or about 0.01% to about 2%, by weight, based on the weight of the copolymer.

3. The polymer composition of claim 1, wherein:

(i) $R^2$, $R^3$, $R^5$, $R^6$, $R^8$, and $R^9$ are hydrogen, and the first monomer is 3-(6-hydroxy-3-oxo-3H-xanthen-9-yl)propanoic acid, a salt, a hydrate, a salt hydrate, a stereoisomer, a dehydrate, a tautomer, or a derivative thereof—

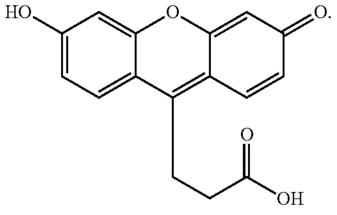 [SMILES: O=C(O)CCc1c2ccc(=O)cc-2oc2cc(O)ccc12]

4. The polymer composition of claim 1, wherein the at least one second monomer—

(i) is selected from the group consisting of an allylsulfonate salt, acrylic acid, vinyl sulfonic acid, a vinyl sulfonate salt, vinyl phosphoric acid, a vinyl phosphonate salt, vinylidene diphosphonic acid or a salt thereof, methacrylic acid, vinyl acetate, vinyl alcohol, vinyl chloride, an unsaturated mono- or di-carboxylic acid or anhydride, styrene-p-sulfonic acid, a styrene sulfonate salt, acrylamido-2-methylpropanesulfonic acid (AMPS), hydroxyphosphonoacetic acid (HPA), a hypophosphorus acid, an acrylamide, a propargyl alcohol of formula HC≡C—$CH_2$—OH, butyr-1,4-diol, and a combination thereof;

(ii) is selected from the group consisting of sodium allylsulfonate, maleic anhydride, maleic acid, fumaric acid, itaconic acid, aconitic acid, mesaconic acid, citraconic acid, crotonic acid, isocrotonic acid, angelic acid, tiglic acid, and a combination thereof;

(iii) comprises sodium allyl sulfonate and at least one of maleic acid, maleic anhydride, or acrylic acid;

(iv) comprises at least one of maleic acid, maleic anhydride, or acrylic acid; or (v) comprises a compound of Formula (II):

Formula (II)

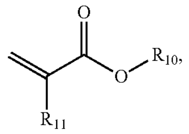

wherein $R^{10}$ and $R^{11}$ are independently selected from the group consisting of hydrogen and alkyl.

5. The polymer composition of claim 1, wherein the first monomer is an end group of the copolymer.

6. A method for preventing or reducing scale formation, the method comprising:

providing a system comprising a fluid in circulation, wherein the fluid comprises a polymer composition of claim 1;

measuring with an analytical technique an amount of the first monomer in the system or the fluid to determine an amount of the polymer composition in the system or the fluid, wherein the measuring is performed periodically or continuously.

* * * * *